(12) United States Patent
Shiba et al.

(10) Patent No.: US 11,846,632 B2
(45) Date of Patent: Dec. 19, 2023

(54) SAMPLE MEASUREMENT DEVICE AND SAMPLE MEASUREMENT METHOD

(71) Applicant: SYSMEX CORPORATION, Kobe (JP)

(72) Inventors: Masaki Shiba, Kobe (JP); Hironori Katsumi, Kobe (JP); Tsuyoshi Fukuzaki, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 319 days.

(21) Appl. No.: 16/232,145

(22) Filed: Dec. 26, 2018

(65) Prior Publication Data
US 2019/0204304 A1 Jul. 4, 2019

(30) Foreign Application Priority Data
Dec. 28, 2017 (JP) .................................. 2017-253155

(51) Int. Cl.
*G01N 33/53* (2006.01)
*G01N 35/10* (2006.01)
(Continued)

(52) U.S. Cl.
CPC ......... *G01N 33/5302* (2013.01); *G01N 21/76* (2013.01); *G01N 33/53* (2013.01);
(Continued)

(58) Field of Classification Search
CPC ............... G01N 33/5302; G01N 33/86; G01N 33/6854; G01N 33/53; G01N 33/54306;
(Continued)

(56) References Cited

U.S. PATENT DOCUMENTS 5,474,744 A * 12/1995 Lerch ................. G01N 35/1004
73/864.22
2002/0085959 A1 * 7/2002 Carey ..................... B01L 3/508
422/400
(Continued)

FOREIGN PATENT DOCUMENTS

| CN | 102313816 A | 1/2012 |
| CN | 102348988 A | 2/2012 |

(Continued)

OTHER PUBLICATIONS

Translation of JPH11271329A, Kikuchi Takahiro, Oct. 8, 1999 (Year: 1999).*
(Continued)

*Primary Examiner* — Maris R Kessel
*Assistant Examiner* — Henry H Nguyen
(74) *Attorney, Agent, or Firm* — METROLEX IP LAW GROUP, PLLC

(57) ABSTRACT

A sample measurement device including: a dispensing mechanism that includes a nozzle capable of penetrating through a plug body that closes a sample container and of aspirating and discharging a sample housed in the sample container, and that dispenses the sample into a disposable container from the sample container through the nozzle; a cleaning mechanism that cleans the nozzle; and a first measurement section that performs measurement for an immunological test of the sample dispensed by the dispensing mechanism.

16 Claims, 16 Drawing Sheets

(51) Int. Cl.
*G01N 21/76* (2006.01)
*G01N 33/86* (2006.01)
*G01N 33/68* (2006.01)
*G01N 33/543* (2006.01)
*G01N 21/82* (2006.01)

(52) U.S. Cl.
CPC ... *G01N 33/54306* (2013.01); *G01N 33/6854* (2013.01); *G01N 33/86* (2013.01); *G01N 35/1004* (2013.01); *G01N 35/1009* (2013.01); *G01N 35/1079* (2013.01); *G01N 2021/825* (2013.01)

(58) Field of Classification Search
CPC ........... G01N 35/1079; G01N 35/1004; G01N 35/1009; G01N 21/76; G01N 2021/825; G01N 35/00603; G01N 35/0095
See application file for complete search history.

(56) References Cited

U.S. PATENT DOCUMENTS

| | | | |
|---|---|---|---|
| 2010/0108101 A1* | 5/2010 | Shibata | B01L 3/0293 134/22.11 |
| 2014/0106467 A1 | 4/2014 | Hutter et al. | |
| 2014/0178251 A1* | 6/2014 | Yamada | G01N 35/025 422/67 |
| 2014/0290706 A1* | 10/2014 | Ravalico | G01N 35/1004 134/169 R |
| 2017/0315047 A1 | 11/2017 | Yamada | |

FOREIGN PATENT DOCUMENTS

| | | | |
|---|---|---|---|
| CN | 104350386 A | 2/2015 | |
| EP | 0502638 A2 | 9/1992 | |
| JP | S62-73251 U | 5/1987 | |
| JP | S63-70169 A | 3/1988 | |
| JP | H4-328467 A | 11/1992 | |
| JP | H06242127 A | 9/1994 | |
| JP | H07218513 A | 8/1995 | |
| JP | H11271329 A * | 10/1999 | |
| JP | 2001-013151 A | 1/2001 | |
| JP | 2001-272409 A | 10/2001 | |
| JP | 2002-148181 A | 5/2002 | |
| JP | 2003-185672 A | 7/2003 | |
| JP | 2005-527839 A | 9/2005 | |
| JP | 2010-133827 A | 6/2010 | |
| JP | 2010133727 A | 6/2010 | |
| JP | 2010-256050 A | 11/2010 | |
| JP | 2012-042294 A | 3/2012 | |
| JP | 2014-122852 A | 7/2014 | |
| JP | 2017-096895 A | 6/2017 | |
| JP | 2017-198625 A | 11/2017 | |
| WO | WO-2010021172 A1 * | 2/2010 | ........... G01N 35/025 |
| WO | 2016/170994 A1 | 10/2016 | |

OTHER PUBLICATIONS

Translation of WO2010021172A1, Ushikubo, Masao, Feb. 25, 2010 (Year: 2010).*
The extended European search report ("EESR") dated Jun. 6, 2019 in a counterpart European patent application.
A Office Action dated Jun. 29, 2021 in a counterpart Japanese patent application, with English translation.
The Office Action (JPOA) dated Dec. 7, 2021 in a counterpart Japanese patent application, with English translation.
The Office Action (CNOA) dated Mar. 30, 2022 in a counterpart Chinese patent application, with English translation.
The Communication pursuant to Article 94(3) EPC dated Apr. 25, 2022 in a counterpart European patent application.
The Office Action (JPOA) dated Mar. 29, 2022 in a counterpart Japanese patent application, with English translation.
The Decision of Refusal dated Jul. 19, 2022 in a counterpart Japanese patent application, with English translation.
The Decision of Dismissal of Amendment dated Jul. 19, 2022 in a counterpart Japanese patent application, with English translation.
The Office Action (CNOA) dated Nov. 16, 2022 in a counterpart Chinese patent application, with English translation.
The Rejection Decision dated Feb. 28, 2023 in a counterpart Chinese patent application, with English translation.
The Communication pursuant to Article 94 (3) EPC dated Jun. 2, 2023 in a counterpart European patent application.
The Office Action (JPOA) dated Jun. 13, 2023 in a related Japanese patent application, with English translation.
The Office Action (JPOA) dated Aug. 22, 2023 in a counterpart Japanese patent application.
The Office Action dated Aug. 29, 2023 in a counterpart Australian patent application.
An Office Action dated Sep. 26, 2023 in a counterpart Chinese patent application.
A Communication pursuant to Article 94(3) EPC dated Oct. 19, 2023 in a counterpart European patent application.

* cited by examiner

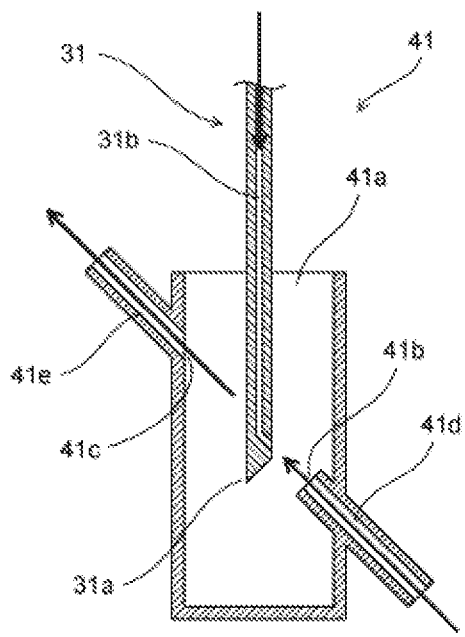
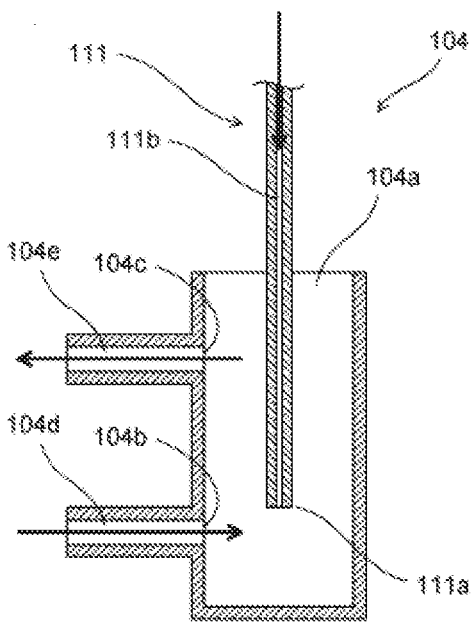
FIG. 7A  FIG. 7B
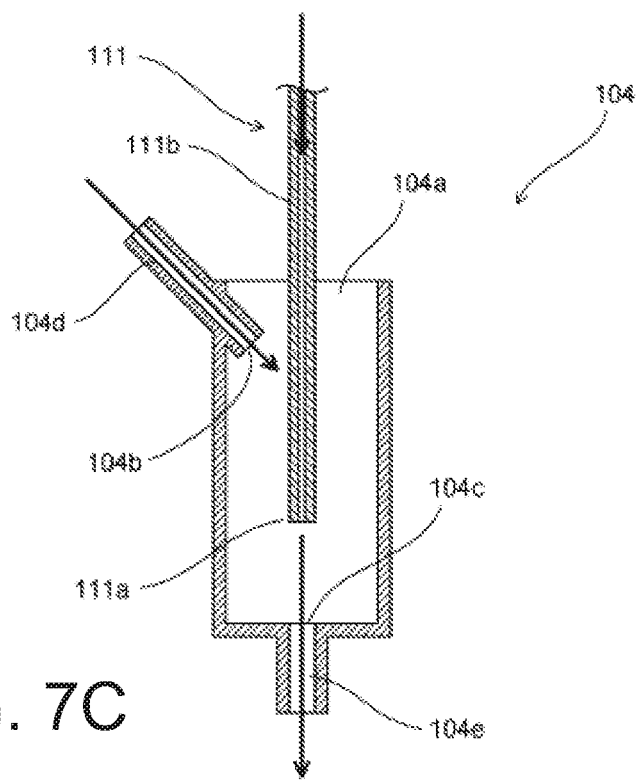
FIG. 7C

MEASUREMENT FOR BLOOD COAGULATION TEST

MEASUREMENT FOR IMMUNOLOGICAL TEST

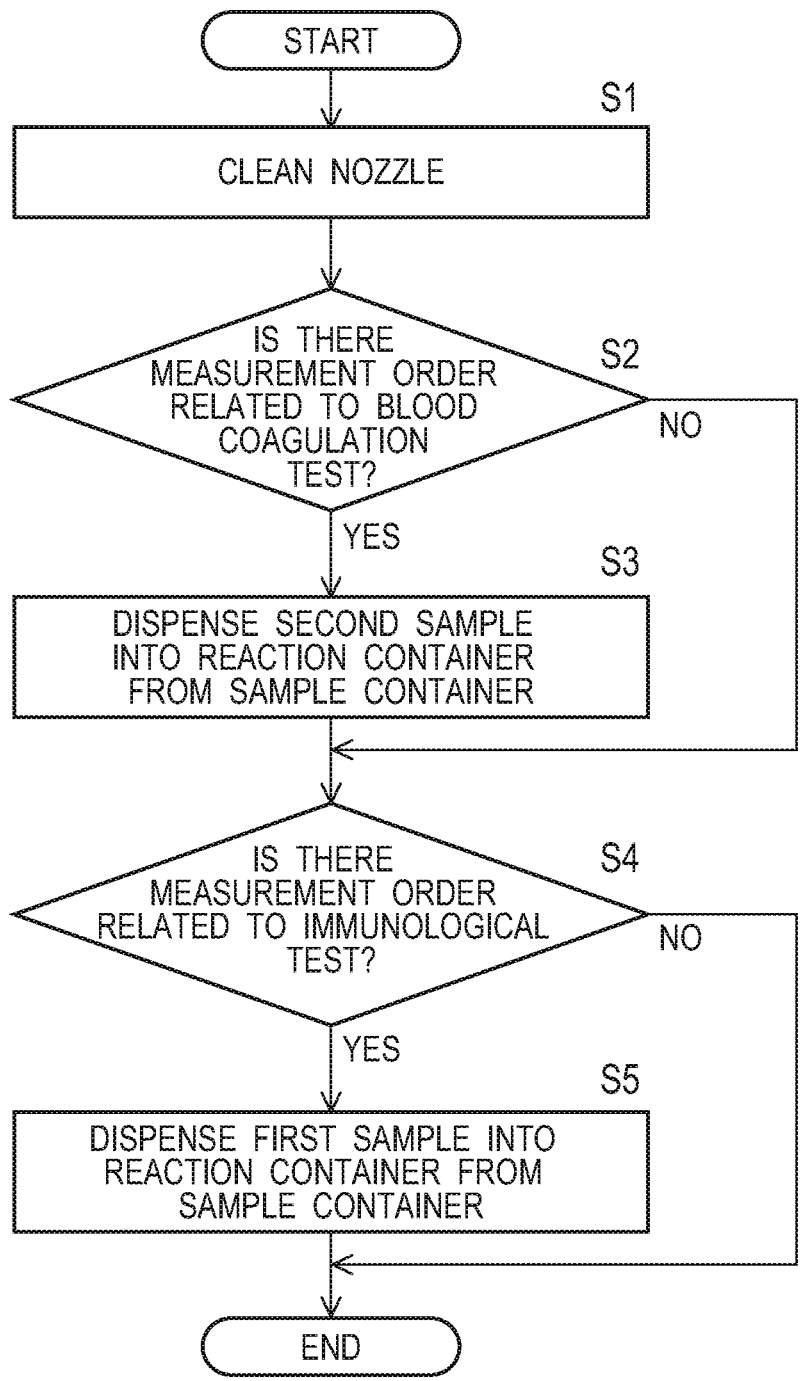

SAMPLE MEASUREMENT DEVICE AND SAMPLE MEASUREMENT METHOD

CROSS REFERENCE TO RELATED APPLICATIONS

This application claims priority based on 35 USC 119 from prior Japanese Patent Application No. 2017-253155 filed on Dec. 28, 2017, entitled "SAMPLE MEASUREMENT DEVICE AND SAMPLE MEASUREMENT METHOD", the entire contents of which are incorporated herein by reference.

BACKGROUND

The disclosure relates to a sample measurement device and a sample measurement method for measuring a sample.

There has been known an analyzer that performs measurement for an immunological test. For example, Japanese Patent Application Publication No. 2010-133827 (Patent Literature 1) discloses an analyzer that dispenses a sample by using a disposable tip to avoid mixing of different samples, what is termed carry-over, in measurement for an immunological test. As illustrated in FIG. 16, in this analyzer, a disposable tip loaded in a tip loading unit 401 is attached to a connecting tube of a sample dispenser 402 to aspirate a sample from a sample container 403. The sample is aspirated at a sample aspirating position 404. The aspirated sample is dispensed into a reaction container held on an immune reaction table 405. After the sample is dispensed, the disposable tip is disposed of into a disposal box in the tip loading unit 401.

A sample container that houses a sample is usually closed with a plug body. Therefore, in the measurement for an immunological test, an operator, for example, removes the plug body from the sample container, and feeds the sample container into the analyzer with the top of the sample container opened. In this case, the operator needs to previously go to the cumbersome work of removing the plug body from the sample container.

SUMMARY

A first aspect of the disclosure is a sample measurement device including: a dispensing mechanism that includes a nozzle capable of penetrating through a plug body that closes a sample container and of aspirating and discharging a sample housed in the sample container, and that dispenses the sample into a disposable container from the sample container through the nozzle; a cleaning mechanism that cleans the nozzle; and a first measurement section that performs measurement for an immunological test of the sample dispensed by the dispensing mechanism.

A second aspect of the disclosure is a sample measurement method including: cleaning a nozzle capable of penetrating through a plug body that closes a sample container and of aspirating and discharging a sample housed in the sample container; dispensing the sample into a disposable container from the sample container through the cleaned nozzle; and performing measurement for an immunological test of the dispensed sample.

A third aspect of the disclosure is a sample measurement device including: a dispensing mechanism that includes a nozzle capable of penetrating through a plug body that closes a sample container and of aspirating and discharging a sample housed in the sample container, and that dispenses the sample into a disposable container from the sample container through the nozzle; a first measurement section that performs measurement for a first test of the sample dispensed by the dispensing mechanism; and a second measurement section that performs measurement for a second test different from the first test of the sample dispensed by the dispensing mechanism.

BRIEF DESCRIPTION OF DRAWINGS

FIG. 7A is a diagram schematically illustrating a cross-sectional view of a configuration of a cleaning tank according to a modified example, FIG. 7B is a diagram schematically illustrating a cross-sectional view of a configuration of a cleaning tank for cleaning a dispensing mechanism that aspirates a sample from a sample aspirating position on the right side according to an embodiment, and FIG. 7C is a diagram schematically illustrating a cross-sectional view of a configuration of a cleaning tank for cleaning a dispensing mechanism that aspirates a sample from a sample aspirating position on the right side according to a modified example;

FIG. 14 is a flowchart illustrating processing related to a dispensing mechanism according to an embodiment;

DETAILED DESCRIPTION

Figure 1:
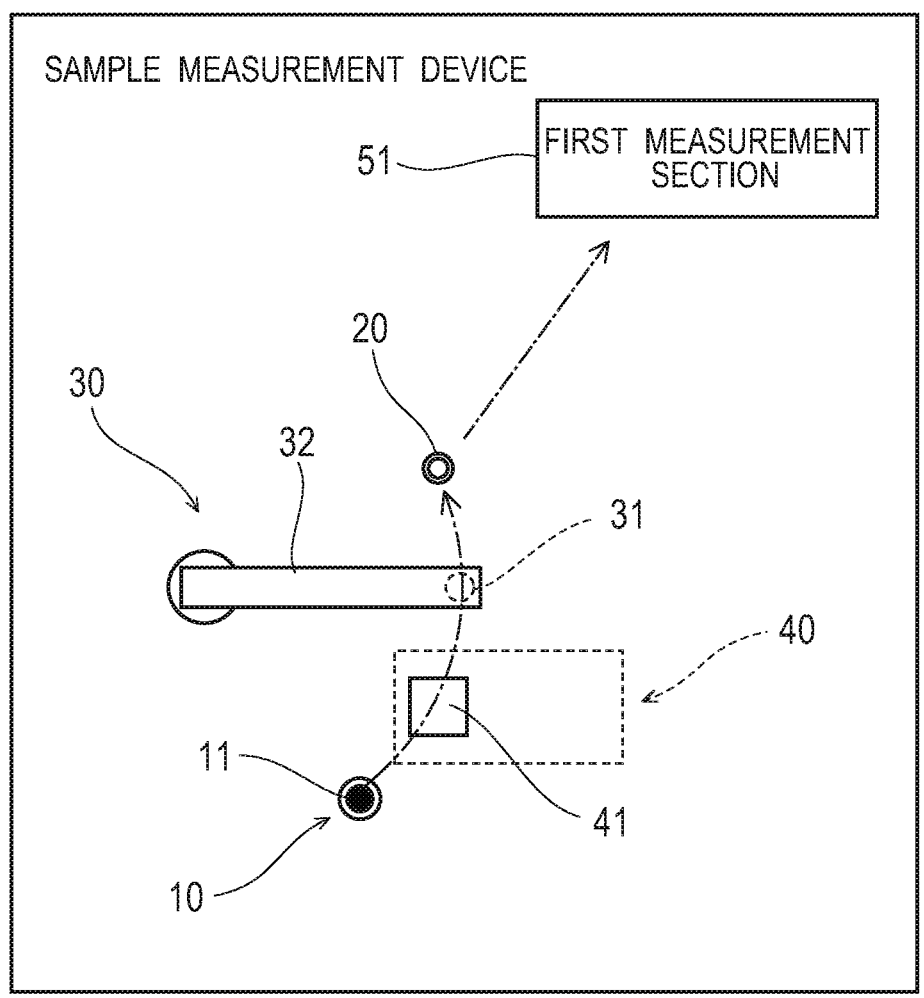
FIG. 1 is a diagram schematically illustrating a view of a general configuration of a sample measurement device according to an embodiment.

Embodiments are explained with referring to drawings. In the respective drawings referenced herein, the same constitutions are designated by the same reference numerals and duplicate explanation concerning the same constitutions is basically omitted. All of the drawings are provided to illustrate the respective examples only. No dimensional proportions in the drawings shall impose a restriction on the embodiments. For this reason, specific dimensions and the like should be interpreted with the following descriptions taken into consideration. In addition, the drawings include parts whose dimensional relationship and ratio are different from one drawing to another.

With reference to FIG. 1, a summary of a sample measurement device according to an embodiment is described. In FIG. 1, X, Y, and Z axes are orthogonal to each other. An X-axis forward direction corresponds to a leftward direction, a Y-axis forward direction corresponds to a backward direction, and a Z-axis forward direction corresponds to a vertically downward direction. Note that, in the other drawings, the X, Y, and Z axes are set in the same manner as FIG. 1.

The sample measurement device 100 measures a sample housed in a sample container 10 closed with a plug body 11. The sample container 10 houses the sample therein and has its top sealed with the plug body 11. The plug body 11 is made of elastic synthetic resin, for example.

The sample measurement device 100 includes a dispensing mechanism 30, a cleaning mechanism 40, and a first measurement section 51. The dispensing mechanism 30 includes a nozzle 31 and an arm 32. The nozzle 31 is configured to be capable of penetrating through the plug body 11 and aspirating and discharging the sample. The nozzle 31 is an aspiration tube. The nozzle 31 is provided at an end of the arm 32, and the arm 32 is configured to be turnable. The dispensing mechanism 30 dispenses the sample from the sample container 10 into a disposable container 20 by using the nozzle 31. The cleaning mechanism 40 includes a cleaning tank 41. The cleaning mechanism 40 also includes a mechanism that supplies a cleaning liquid to the cleaning tank 41 and a mechanism that supplies the cleaning liquid into the nozzle 31. The cleaning mechanism 40 cleans the nozzle 31.

When the sample container 10 is located at a predetermined position, the dispensing mechanism 30 turns the arm 32 to locate the nozzle 31 immediately above the sample container 10. Then, the dispensing mechanism 30 lowers the arm 32 to lower the nozzle 31. Thus, the tip of the nozzle 31 penetrates downward through the plug body 11. Thereafter, the dispensing mechanism 30 aspirates the sample in the sample container 10 through the tip of the nozzle 31.

Once the sample is aspirated, the dispensing mechanism 30 lifts the arm 32 to lift the nozzle 31. Accordingly, the nozzle 31 is pulled out of the plug body 11. Subsequently, the dispensing mechanism 30 turns the arm 32 to locate the nozzle 31 immediately above the disposable container 20. The disposable container 20 is a container having its top open. The dispensing mechanism 30 lowers the arm 32 to insert the tip of the nozzle 31 into another container 20. The dispensing mechanism 30 discharges the sample aspirated from the sample container 10 into the disposable container 20. The disposable container 20 is a different container from the sample container 10.

Thereafter, the sample discharged into the disposable container 20 is transferred by the disposable container 20 and a container into which the sample is transferred from the disposable container 20, and has a predetermined reagent added thereto. Then, the sample having the predetermined reagent added thereto is transferred to the first measurement section 51. The first measurement section 51 performs measurement for a more highly sensitive test than a test performed by the second measurement section 52. To be more specific, the first measurement section 51 performs measurement for an immunological test of a sample. The measurement for the immunological test includes measurement of immunological analysis items, measurement by immunological reaction, and the like. The measurement for the immunological test in the embodiment is measurement using antigen-antibody reaction.

Upon completion of the dispensing into the disposable container 20 from the sample container 10, the dispensing mechanism 30 turns and lowers the arm 32 to insert the tip of the nozzle 31 into the cleaning tank 41. Then, the cleaning mechanism 40 causes the cleaning liquid to flow at high pressure into the nozzle 31 and discharges the cleaning liquid from the tip of the nozzle 31. The cleaning mechanism 40 also supplies the cleaning liquid to the cleaning tank 41. The cleaning tank 41 is provided with a discharge port for discharging the cleaning liquid discharged into the cleaning tank 41. Thus, the inner and outer peripheral surfaces of the nozzle 31 are cleaned. Such cleaning of the nozzle 31 is performed upon every aspiration of a different sample.

Since the sample is dispensed directly from the sample container 10 through the nozzle 31 as described above, an operator needs not remove the plug body 11 from the sample container 10. Thus, the measurement for the immunological test can be smoothly performed.

Meanwhile, accidental mixing of another sample into a measurement target sample is called carry-over. When such carry-over occurs, an adequate measurement result can no longer be obtained. The measurement for the immunological test is measurement for a highly sensitive test, which is likely to have carry-over problem and has a high carry-over avoidance level. With the above configuration, the nozzle 31 that dispenses the sample is cleaned by the cleaning mechanism 40. Thus, the influence of carry-over can be reduced in the measurement for the immunological test. Moreover, since the disposable container 20 into which the sample is dispensed is a disposable container, the disposable container 20 is replaced on a sample-by-sample basis, for example. This enables avoidance of carry-over, which may be caused by mixing of a different sample through the disposable container 20. Therefore, the measurement for the immunological test can be properly performed.

<Specific Configuration>

A specific configuration of the sample measurement device 100 is described below.

Figure 2:
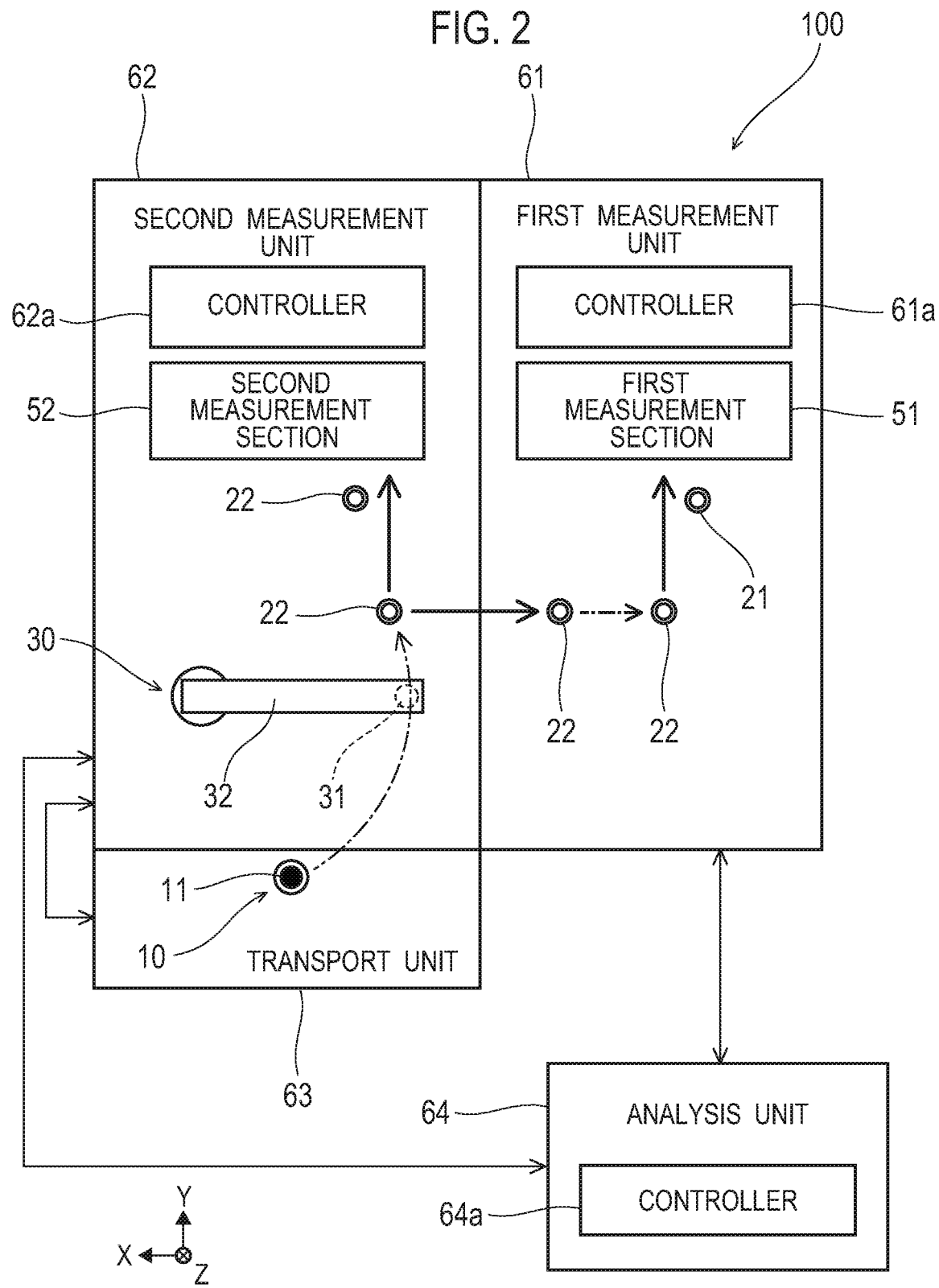
FIG. 2 is a diagram illustrating a view of a specific configuration of the sample measurement device according to an embodiment.

As illustrated in FIG. 2, the sample measurement device 100 includes a first measurement unit 61, a second measurement unit 62, a transport unit 63, and an analysis unit 64. The first measurement unit 61 is communicably connected to the analysis unit 64. The second measurement unit 62 is communicably connected to the transport unit 63 and the analysis unit 64.

The first measurement unit 61 includes a controller 61a and a first measurement section 51 that performs measurement for an immunological test. The controller 61a controls the respective parts of the first measurement unit 61. The controller 61a includes a CPU and a microcomputer, for example. The second measurement unit 62 includes a controller 62a, a dispensing mechanism 30, and a second measurement section 52 that performs measurement for a blood coagulation test. The controller 62a controls the respective parts of the second measurement unit 62. The controller 62a includes the CPU and a microcomputer, for example. The transport unit 63 includes a mechanism to transport the sample container 10 to the second measurement unit 62. The analysis unit 64 includes a personal computer, for example. The analysis unit 64 includes a controller 64a. The controller 64a includes the CPU, for example.

When one sample is measured by both of the first and second measurement section 51 and 52, the dispensing mechanism 30 dispenses the sample in the sample container 10 into two new reaction containers 22. To be more specific, the dispensing mechanism 30 aspirates the sample from the sample container 10 and repeats twice a dispensing operation of discharging the aspirated sample into the new reaction containers 22. The sample first dispensed into the reaction container 22 is the sample to be measured by the second measurement section 52, while the sample dispensed next into the reaction container 22 is the sample to be measured by the first measurement section 51. The sample dispensed into the reaction container 22 in this case is plasma.

When measurement of one sample is performed only by the first measurement section 51, the dispensing mechanism 30 dispenses the sample in the sample container 10 into one new reaction container 22. The sample dispensed into the reaction container 22 in this case is plasma or serum. When measurement of one sample is performed only by the second measurement section 52, the dispensing mechanism 30 dispenses the sample in the sample container 10 into one new reaction container 22. The sample dispensed into the reaction container 22 in this case is plasma.

Note that the sample dispensed into the reaction container 22 may be a body fluid, such as whole blood, urine, lymph fluid, and body cavity fluid, for example. When the sample dispensed into the reaction container 22 is whole blood, processing for purifying plasma or serum from the whole blood dispensed into the reaction container 22 is performed.

The reaction container 22 is a container, so-called cuvette, having a top opening. The reaction container 22 is a disposable container for measurement by the second measurement section 52 in the second measurement unit 62, which is replaced on a sample-by-sample basis. The reaction container 22 corresponds to the disposable container 20 in FIG. 1.

The second measurement unit 62 transfers the reaction container 22, into which the sample to be measured by the first measurement section 51 is dispensed, to the first measurement unit 61. The first measurement unit 61 moves the first sample in the reaction container 22 transferred from the second measurement unit 62 to the reaction container 21. The reaction container 21 is a container, so-called cuvette, having a top opening. The reaction container 21 is a disposable container for measurement by the first measurement section 51 in the first measurement unit 61, which is replaced on a sample-by-sample basis. The first measurement unit 61 prepares a measurement specimen by adding a predetermined reagent to the reaction container 21 into which the first sample is dispensed, and then transfers the reaction container 21 housing the measurement specimen to the first measurement section 51. The first measurement section 51 measures light generated from the measurement specimen in the reaction container 21, that is, chemiluminescence based on a test substance contained in the first sample. The controller 61a generates measurement data based on the light measured by the first measurement section 51.

Here, the chemiluminescence is light emitted using energy generated by chemical reaction, for example, light emitted when molecules are excited by chemical reaction into an excited state and then return to the ground state. The chemiluminescence measured by the first measurement section 51 in the embodiment is light based on chemiluminescent enzyme immunoassay (CLEIA), which is light generated by reaction between an enzyme and a substrate. Note that the chemiluminescence measured by the first measurement section 51 may be, for example, light based on chemiluminescent immunoassay (CLIA), electrochemiluminescent immunoassay (ECLIA), fluorescent enzyme immunoassay (FEIA), luminescent oxygen channeling immunoassay (LOCI), bioluminescent enzyme immunoassay (BLEIA), or the like.

The second measurement unit 62 transfers the reaction container 22 to the second measurement section 52, the reaction container 22 having the sample dispensed thereinto for measurement by the second measurement section 52. In this event, the second measurement unit 62 prepares a measurement specimen by adding a predetermined reagent to the reaction container 22, and then transfers the reaction container 22 housing the measurement specimen to the second measurement section 52. The second measurement section 52 irradiates the measurement specimen in the reaction container 22 with light, and measures light transmitted through the measurement specimen or light scattered by the measurement specimen. The measurement principle for the second measurement section 52 is, for example, a coagulation method, a synthetic substrate method, immunonephelometry, an agglutination method, and the like. The controller 62a generates measurement data based on the light measured by the second measurement section 52.

The controller 64a in the analysis unit 64 performs immunological test-related analysis based on the measurement data generated by the first measurement unit 61. To be more specific, the controller 64a performs analysis for analysis items such as HBs antigen, HBs antibody, HBc antibody, HBe antigen, HBe antibody, HCV antibody, TP antibody, HTLV antibody, HIV antigen and antibody, TAT, PIC, TM, tPAI/c, TSH, FT3, and FT4.

The controller 64a also performs blood coagulation test-related analysis based on the measurement data generated by the second measurement unit 62. To be more specific, the controller 64a performs analysis for analysis items such as PT, APTT, Fbg, extrinsic coagulation factor, intrinsic coagulation factor, coagulation factor XIII, HpT, TTO, FDP, D-dimer, PIC, FM, ATIII, Plg, APL, PC, VWF:Ag, VWF:RCo, ADP, collagen, and epinephrine.

Note that the second measurement unit 62 may perform measurement for a test different from a blood coagulation test. For example, the second measurement unit 62 may perform biochemical test-related measurement. In this case, the controller 64a performs biochemical test-related analysis based on the measurement data generated by the second measurement unit 62. To be more specific, the controller 64a performs analysis for analysis items such as T-BIL, D-BIL, AST, ALT, ALP, LDH, γ-GTP, T-CHO, CRE, and CK.

Although the dispensing mechanism 30 is positioned closer to the second measurement section 52 than to the first measurement section 51 in the sample measurement device 100, as illustrated in FIG. 2, in the embodiment, the dispensing mechanism 30 may also be positioned closer to the first measurement section 51 than to the second measurement section 52. Moreover, the transport unit 63 may be positioned in front of the first measurement unit 61, while the dispensing mechanism 30 may be positioned inside the first measurement unit 61.

Figure 3:
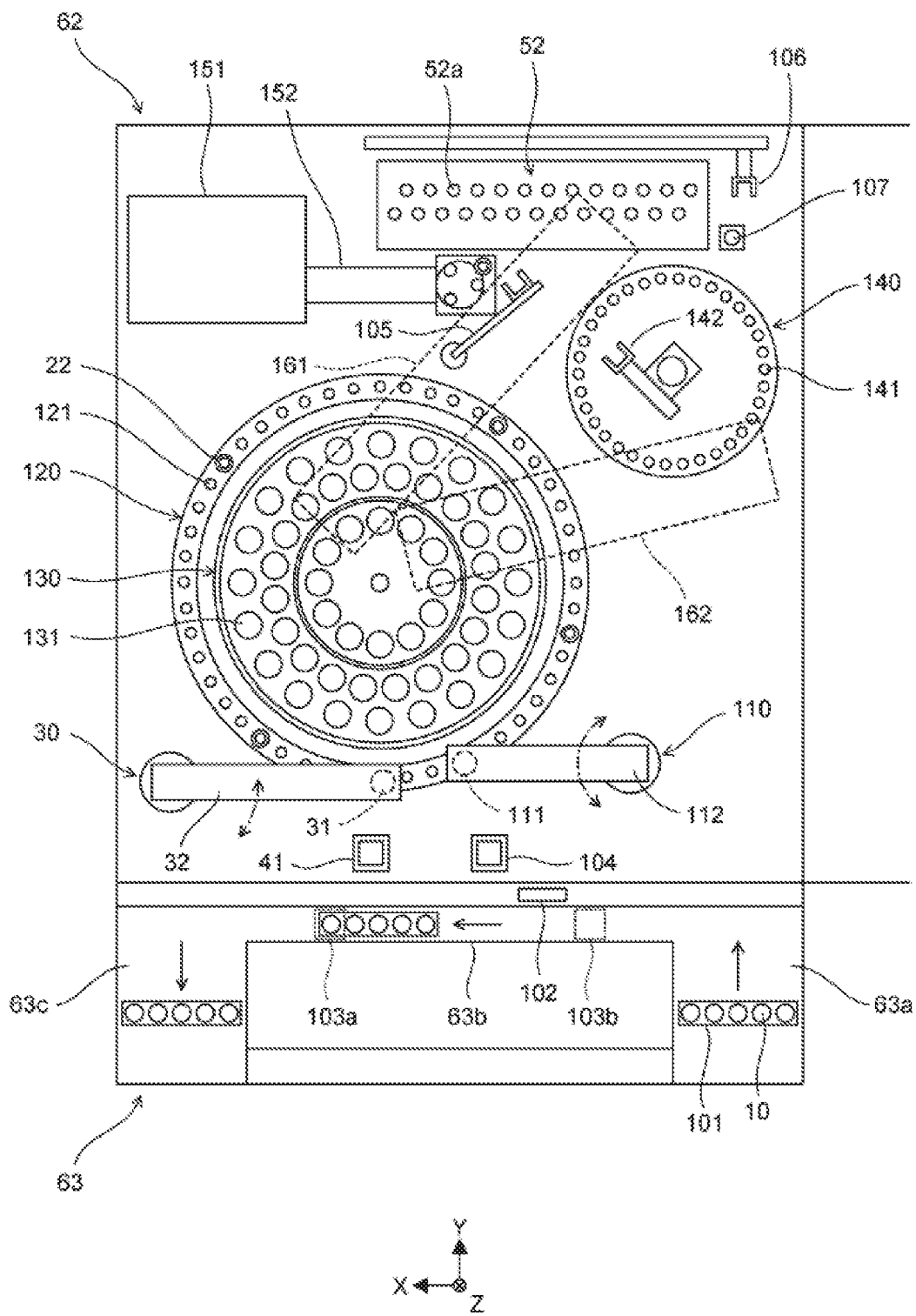
FIG. 3 is a diagram schematically illustrating a view of a configuration of a second measurement unit and a transport unit according to an embodiment.

As illustrated in FIG. 3, the transport unit 63 includes a rack setting part 63a, a rack transporter 63b, and a rack collector 63c. The rack setting part 63a and the rack collector 63c are connected to the right end and left end of the rack transporter 63b, respectively. A bar code reader 102 is provided behind the rack transporter 63b. An operator positions a sample rack 101 having the sample containers 10 set therein in the rack setting part 63a.

Figure 4A:
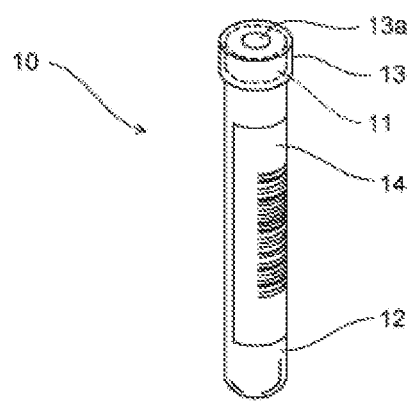
FIG. 4A is a diagram schematically illustrating a perspective view of a configuration of a sample container according to an embodiment.
Figure 4B:
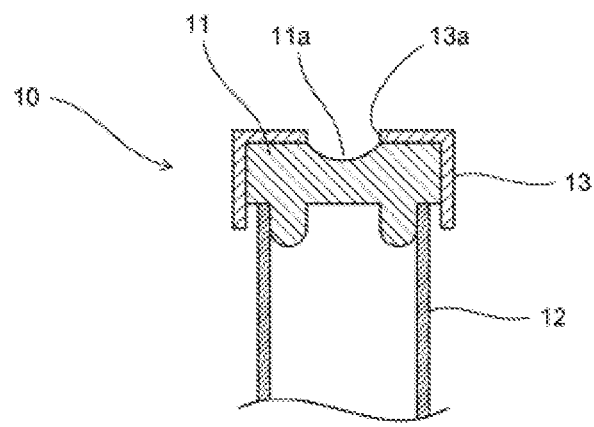
FIG. 4B is a diagram schematically illustrating a cross-sectional view of the configuration of the sample container according to an embodiment.

As illustrated in FIGS. 4A and 4B, the sample container 10 includes the plug body 11, a body part 12, a lid part 13, and a bar code label 14. The body part 12 is a blood collection tube made of translucent glass or synthetic resin, and houses a sample. The plug body 11 is made of elastic synthetic resin or the like as described above. The plug body 11 seals the opening in the upper end of the body part 12 housing the sample. The plug body 11 has a recess 11a formed in its upper surface. The lid part 13 is made of plastic and covers the plug body 11 from above, which is attached to the body part 12. A vertically penetrating hole 13a is formed in the center of the lid part 13. The bar code label 14 is attached to the side of the body part 12. A bar code indicating a sample ID is printed on the bar code label 14. The sample ID is information capable of individually identifying the sample.

Figure 4C:
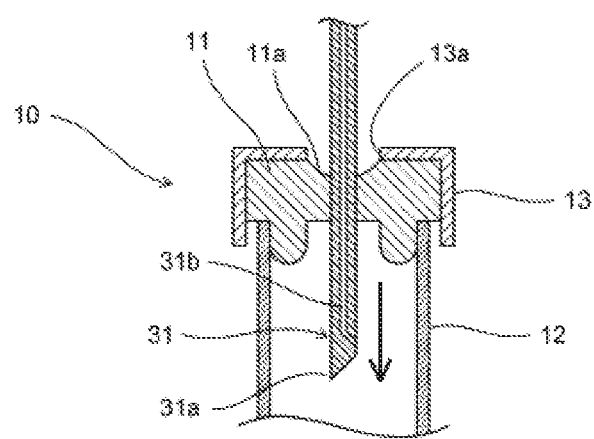
FIG. 4C is a diagram schematically illustrating a cross-sectional view of a state where a nozzle penetrates through the sample container according to an embodiment.

As illustrated in FIG. 4C, the nozzle 31 is a narrow rod-shaped member made of metal. The nozzle has the sharp tip 31a that allows the nozzle 31 to easily penetrate through the plug body 11. A flow path 31b in the nozzle 31 extends vertically along with a direction in which the nozzle 31 extends, and is connected to the outside of the nozzle 31 from the side of the nozzle 31 near the tip 31a. When the nozzle 31 aspirates the sample in the sample container 10, the tip 31a of the nozzle 31 is located in the recess 11a of the plug body 11 through the hole 13a formed in the lid part 13. Then, as the nozzle 31 is moved downward, the tip 31a penetrates through the plug body 11, and the tip 31a of the nozzle 31 is located in the body part 12. Thus, the sample in the sample container 10 can be aspirated.

Referring back to FIG. 3, the transport unit 63 sends the sample rack 101 positioned in the rack setting part 63a to the right end of the rack transporter 63b and further to in front of the bar code reader 102. The bar code reader 102 reads the bar code from the bar code label 14 on the sample container 10 to acquire the sample ID. The acquired sample ID is transmitted to the analysis unit 64 to acquire a measurement order for the sample.

Subsequently, the transport unit 63 transports the sample rack 101 carrying the sample containers 10 to sequentially locate the sample containers 10 at a sample aspirating position 103a or a sample aspirating position 103b. The sample aspirating position 103a is a position for the dispensing mechanism 30 to aspirate the sample, while the sample aspirating position 103b is a position for a dispensing mechanism 110 to be described later to aspirate the sample. Upon completion of the sample aspiration for all the sample containers 10 carried by the sample rack 101, the transport unit 63 transports the sample rack 101 to the rack collector 63c.

The second measurement unit 62 includes the dispensing mechanisms 30 and 110, cleaning tanks 41 and 104, a reaction container table 120, a reagent table 130, a heating table 140, a reaction container housing section 151, a reaction container feeder 152, transfer sections 105 and 106, reagent dispensers 161 and 162, the second measurement section 52, and a disposal port 107.

Figure 5:
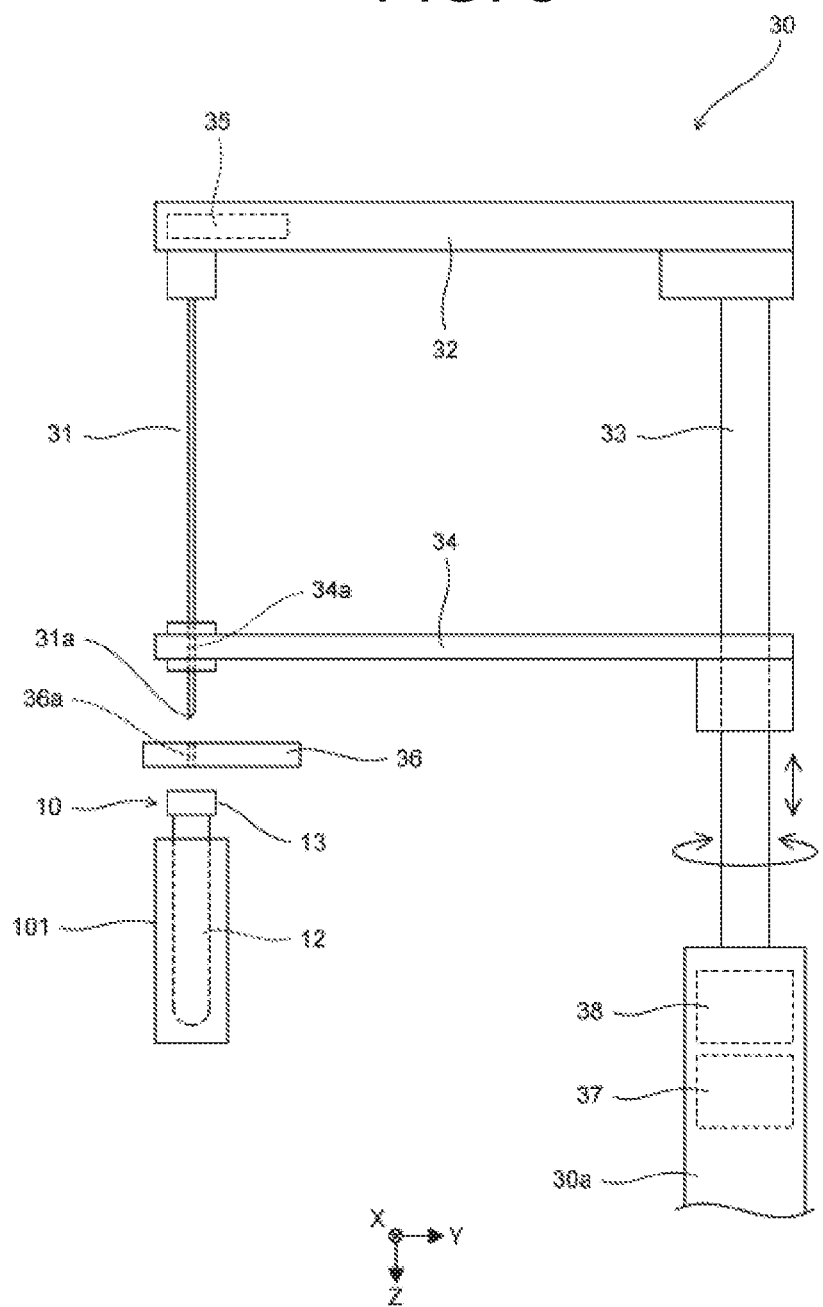
FIG. 5 is a diagram schematically illustrating a side view of a configuration of a dispensing mechanism according to an embodiment.

As illustrated in FIG. 5, the dispensing mechanism 30 includes a main body part 30a, the nozzle 31, the arm 32, a shaft part 33, a guide member 34, and a sensor 35. FIG. 5 illustrates, besides the dispensing mechanism 30, the sample container 10 located at the sample aspirating position 103a and a cleaner 36 provided immediately above the sample aspirating position 103a.

The main body part 30a includes a drive section 37 to move the shaft part 33 in the Z-axis direction and a drive section 38 to rotate the shaft part 33 about the Z-axis direction. The drive sections 37 and 38 each include a stepping motor. The shaft part 33 supports the arm 32. The nozzle 31 is positioned facing downward at the end of the arm 32. The guide member 34 can be rotated along with the rotation of the shaft part 33, and is positioned onto the shaft part 33 so as not to change the position in the Z-axis direction. The guide member 34 has a vertically penetrating hole 34a formed at its tip, and the nozzle 31 is inserted into this hole 34a. The hole 34a limits the movement direction of the nozzle 31 to the Z-axis direction. The sensor 35 is a sensor that senses the tip 31a of the nozzle 31 coming into contact with the liquid surface. The sensor 35 includes a capacitance sensor, for example.

The cleaner 36 has a vertically penetrating passage 36a. The cleaner 36 is arranged such that the nozzle 31 passes through the passage 36a when the nozzle 31 aspirates the sample from the sample container 10. The cleaner 36 performs basic cleaning of the nozzle 31 by discharging and aspirating a cleaning liquid inside when the nozzle 31 passes through the passage 36a.

For aspiration of the sample, the controller 62a controls the dispensing mechanism 30 to lower the nozzle 31 to penetrate through the plug body 11 in a state where sensing by the sensor 35 is turned off, and then further keep lowering the nozzle 31 while turning on the sensing by the sensor 35. Then, the controller 62a detects, through the sensor 35, that the tip 31a of the nozzle 31 comes into the liquid surface of the sample. The controller 62a performs control to cause the dispensing mechanism 30 to aspirate the sample by lowering the nozzle 31 by a predetermined amount after the tip 31a comes into contact with the liquid surface. The lowering amount of the nozzle 31 from the liquid surface in this case is stored in a memory 62b to be described later. To be more specific, the lowering amount of the nozzle 31 from the liquid surface is determined so as to locate the tip 31a above in the sample and also to prevent the nozzle 31 from performing idle aspiration. The memory 62b stores the number of pulses corresponding to the lowering amount, that is, the number of pulses required to lower the nozzle 31 by driving the drive section 37.

Referring back to FIG. 3, the dispensing mechanism 110 includes a nozzle 111 and an arm 112, as in the case of the dispensing mechanism 30, and has the same configuration as that illustrated in FIG. 5.

The dispensing mechanism 30 aspirates the sample from the sample container 10 located at the sample aspirating position 103a. In this event, as described with reference to FIG. 4C, the nozzle 31 is driven downward so as to penetrate through the plug body 11, and a negative pressure is applied to the flow path 31b of the nozzle 31 to aspirate the sample into the flow path 31b. Thereafter, the nozzle 31 is driven upward and the tip 31a of the nozzle 31 is pulled out of the plug body 11. The dispensing mechanism 30 discharges the aspirated sample into a new reaction container 22 held on the reaction container table 120.

Here, as for the sample located at the sample aspirating position 103a, a measurement order to perform measurement for an immunological test by the first measurement unit 61, a measurement order to perform blood coagulation test-related measurement by the second measurement unit 62, or a measurement order to perform measurement by both of the measurement units is set.

When only the measurement order for the immunological test is set, the dispensing mechanism 30 aspirates the sample once from the sample container 10 and discharges the aspirated sample into the reaction container 22 on the reaction container table 120 as a first sample for the measurement for the immunological test. When only the measurement order for the blood coagulation test is set, the dispensing mechanism 30 aspirates the sample once from the sample container 10 and discharges the aspirated sample into the reaction container 22 on the reaction container table 120 as a second sample for the blood coagulation test-related measurement.

When the measurement order is set for both of the immunological test and the blood coagulation test, the dispensing mechanism 30 aspirates the sample in two steps from the sample container 10 and discharges the aspirated sample into the reaction containers 22 on the reaction container table 120. In this event, the dispensing mechanism 30 discharges the sample aspirated first into the reaction container 22 as the second sample for use in the blood coagulation test-related measurement, and discharges the sample aspirated later into the reaction container 22 as the first sample for use in the measurement for the immunological test.

Note that the dispensing mechanism 110 aspirates the sample, for which only the measurement order for the blood coagulation test is set, from the sample container 10 having its top not sealed with the plug body 11. The dispensing mechanism 110 discharges the aspirated sample into the reaction container 22 as the second sample for use in the blood coagulation test-related measurement.

The reaction container table 120 has a ring shape in a plan view and is located outside the reagent table 130. The reaction container table 120 is configured to be rotatable in the circumferential direction. The reaction container table 120 has holding holes 121 for holding the reaction containers 22.

The reaction container housing section 151 houses new reaction containers 22. The reaction container feeder 152 takes the reaction containers 22 one by one from the reaction container housing section 151 and feeds the reaction container 22 taken out to a grabbing position by the transfer section 105. The transfer section 105 grabs the reaction container 22 fed to the grabbing position by the reaction container feeder 152 and sets the reaction container 22 in the holding hole 121 in the reaction container table 120.

Upon completion of dispensing into one sample container 10 located at the sample aspirating position 103a, the dispensing mechanism 30 positions the nozzle 31 in the cleaning tank 41. The nozzle 31 positioned in the cleaning tank 41 is cleaned inside the cleaning tank 41. In this way, the nozzle 31 is cleaned inside the cleaning tank 41 on a sample-by-sample basis. Likewise, upon completion of dispensing into one sample container 10 located at the sample aspirating position 103b, the dispensing mechanism 110 positions the nozzle 111 in the cleaning tank 104. The nozzle 111 positioned in the cleaning tank 104 is cleaned inside the cleaning tank 104. In this way, the nozzle 111 is cleaned inside the cleaning tank 104 on a sample-by-sample basis.

Figure 6A:
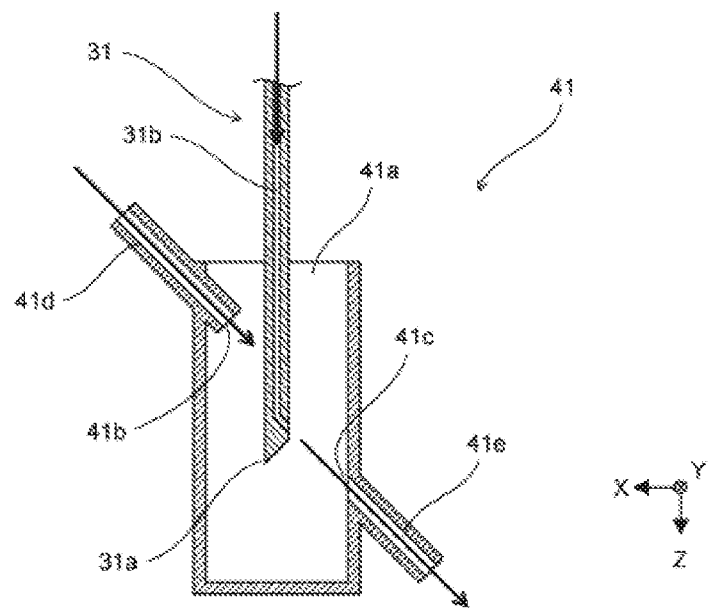
FIG. 6A is a diagram schematically illustrating a cross-sectional view of a configuration of a cleaning tank according to the embodiment.

As illustrated in FIG. 6A, the cleaning tank 41 is a container having the inside open through a top opening 41a. The cleaning tank 41 has an injection port 41b formed in its upper part and has a discharge port 41c formed in its lower part. The injection port 41b is connected to the outside of the cleaning tank 41 through an injection passage 41d. The discharge port 41c is connected to the outside of the cleaning tank 41 through a discharge passage 41e. The injection passage 41d is formed so as to face obliquely downward toward the injection port 41b, while the discharge passage 41e is formed so as to face obliquely upward toward the discharge port 41c.

In cleaning of the nozzle 31, the nozzle 31 is inserted into the cleaning tank 41 from above through the opening 41a. In this event, the nozzle 31 is inserted into the opening 41a in such a manner that the cleaning liquid injected from the injection port 41b spills out over a portion of the outer peripheral surface of the nozzle 31 with which the sample has come into contact. Then, the cleaning liquid is injected into the cleaning tank 41 through the injection passage 41d and the injection port 41b, and is discharged through the discharge port 41c and the discharge passage 41e. Thus, the outer peripheral surface of the nozzle 31 is cleaned. The cleaning liquid also flows through the flow path 31b in the nozzle 31. The cleaning liquid in the flow path 31b is discharged from an outlet of the flow path 31b provided near the tip 31a. Accordingly, an inner peripheral surface of the nozzle 31, that is, the flow path 31b is cleaned. Thus, at least the portions of the inner and outer peripheral surfaces of the nozzle 31, with which the sample has come into contact, are cleaned with the cleaning liquid.

Here, the flow path 31b of the nozzle 31 is cleaned at high pressure with the cleaning liquid. To be more specific, a flow rate of the cleaning liquid flowing through the flow path 31b is increased so as to generate a turbulent flow inside the flow path 31b. Generally, a turbulent flow is considered to be generated when the Reynolds number becomes greater than 4000. Assuming that fluid density is p, fluid flow rate is U, inside diameter of the flow path is d, and viscosity coefficient is p, the Reynolds number Re is calculated according to the following equation.

$$Re = pUd/\mu$$

Figure 6B:
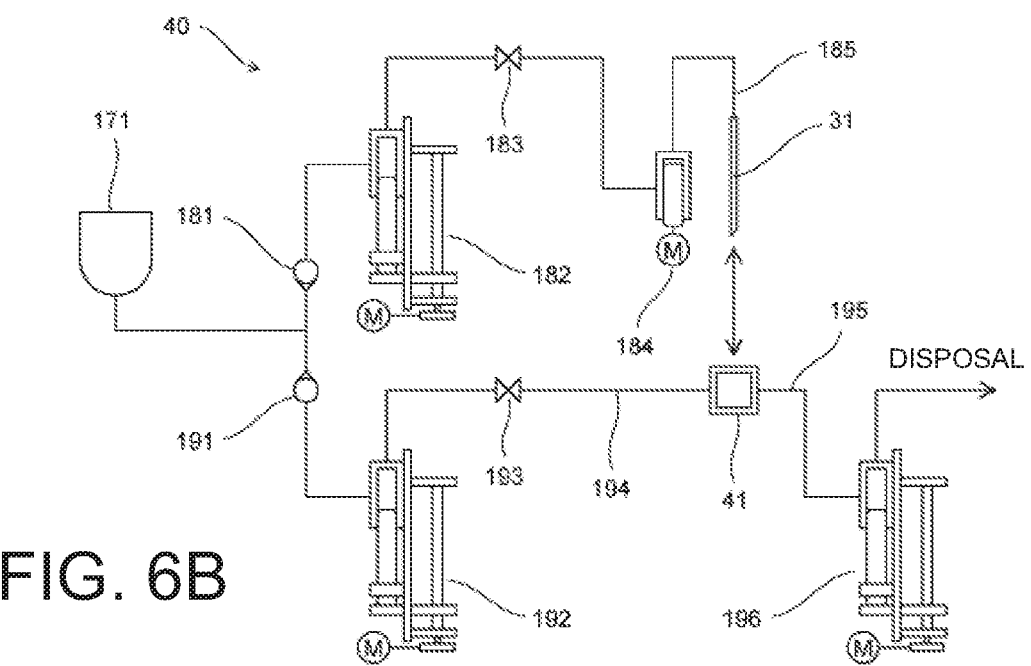
FIG. 6B is a diagram schematically illustrating a view of a configuration of a cleaning mechanism according to an embodiment.

With reference to FIG. 6B, a configuration of the cleaning mechanism 40 is described. As illustrated in FIG. 6B, the cleaning mechanism 40 includes a flow path and a mechanism to allow the cleaning liquid to flow through the flow path 31b of the nozzle 31, and a flow path and a mechanism to allow the cleaning liquid to flow into the cleaning tank 41.

The cleaning liquid is stored in a cleaning liquid chamber 171. The cleaning liquid chamber 171 is connected to a first pump 182 by a flow path through a check valve 181. The first pump 182 includes a syringe capable of sending the cleaning liquid at high pressure. The first pump 182 has its sending side connected to a metering syringe 184 by a flow path through a solenoid valve 183. The metering syringe 184 has its sending side connected to the flow path 31b of the nozzle 31 through a first flow path 185.

Meanwhile, the cleaning liquid chamber 171 is connected to a second pump 192 by a flow path through a check valve 191. The second pump 192 includes a syringe capable of sending the cleaning liquid. The second pump 192 has its sending side connected to the injection passage 41d and the injection port 41b of the cleaning tank 41 by a second flow path 194 through a solenoid valve 193. The discharge port 41c and the discharge passage 41e of the cleaning tank 41 are connected to a third pump 196 through a third flow path 195. The third pump 196 includes a syringe capable of applying a negative pressure to the third flow path 195. The third pump 196 has its sending side connected to a flow path for disposal of the cleaning liquid.

In dispensing the sample with the nozzle 31, the metering syringe 184 takes the sample into the flow path 31b by applying a negative pressure to the first flow path 185, and discharges the sample taken into the flow path 31b by applying a positive pressure to the first flow path 185.

In cleaning the flow path 31b of the nozzle 31, the first pump 182 takes in the cleaning liquid from the cleaning liquid chamber 171 in a state where the solenoid valve 183 is closed. Then, in a state where the solenoid valve 183 is opened, the first pump 182 allows the cleaning liquid taken in to flow into the flow path 31b of the nozzle 31 through the solenoid valve 183, the metering syringe 184, and the first flow path 185. In this event, the flow rate of the cleaning liquid flowing through the flow path 31b is set such that the Reynolds number Re expressed by the above equation becomes greater than 4000, and the first pump 182 is driven to realize this flow rate. Thus, a turbulent flow is generated in the flow path 31b to enhance the cleaning effect inside the flow path 31b. Moreover, cleaning inside the nozzle 31 can be ensured, and thus carry-over due to mixing of different samples through the nozzle 31 can be avoided.

Note that the lower end of the flow path 31b of the nozzle 31 is connected to the outer side surface of the nozzle 31 as illustrated in FIG. 6A, in order to prevent fragments of the plug body 11 from clogging the flow path 31b when the nozzle 31 penetrates through the plug body 11 of the sample container 10. Accordingly, the cleaning liquid flowing through the flow path 31b is discharged to the side of the nozzle 31. The discharge passage 41e for discharging the cleaning liquid extends obliquely downward. In this way, the direction of the cleaning liquid discharged from the flow path 31b coincides with the direction of the discharge passage 41e. Thus, the cleaning liquid discharged from the flow path 31b is smoothly collected to the discharge passage 41e through the discharge port 41c.

To clean the outer peripheral surface of the nozzle 31, the second pump 192 takes in the cleaning liquid from the cleaning liquid chamber 171 in a state where the solenoid valve 193 is closed. Then, in a state where the solenoid valve 193 is opened, the second pump 192 allows the cleaning liquid taken in to flow into the cleaning tank 41 from the injection port 41b of the cleaning tank 41 through the solenoid valve 193 and the second flow path 194. The flow rate of the cleaning liquid flowing through the second flow path 194 is set so as to get just the right amount of cleaning liquid to clean the outer peripheral surface of the nozzle 31. When the cleaning liquid flows into the cleaning tank 41, the third pump 196 is driven to draw the cleaning liquid into the third flow path 195 from the discharge port 41c and the discharge passage 41e. The third pump 196 allows the cleaning liquid drawn into the third flow path 195 to flow into a flow path for disposal.

As illustrated in FIG. 6B, the configuration of the cleaning mechanism 40 enables smooth cleaning of the inner and outer peripheral surfaces of the nozzle 31.

Note that the cleaning tank 41 illustrated in FIG. 6A may be configured as illustrated in FIG. 7A. More specifically, in a cleaning tank 41 illustrated in FIG. 7A, an injection port 41b is formed in the lower part of the cleaning tank 41, and an injection passage 41d is formed so as to face obliquely upward toward the injection port 41b. A discharge port 41c is formed in the upper part of the cleaning tank 41, and a discharge passage 41e is formed so as to face obliquely downward toward the discharge port 41c. Also in this case, the outer peripheral surface of the nozzle 31 is cleaned by discharging the cleaning liquid, which is injected from the injection port 41b, from the discharge port 41c.

As illustrated in FIG. 7B, a cleaning tank 104 is a container having its top open through an opening 104a. The cleaning tank 104 has an injection port 104b formed in its lower part and has a discharge port 104c formed in its upper part. The injection port 104b is connected to the outside of the cleaning tank 104 through an injection passage 104d. The discharge port 104c is connected to the outside of the cleaning tank 104 through a discharge passage 104e. The injection passage 104d and the discharge passage 104e are formed so as to extend in a horizontal direction. A tip 111a of a nozzle 111 is not sharp, and a flow path 111b inside the nozzle 111 extends in a vertical direction.

To clean the nozzle 111, the nozzle 111 is inserted into the cleaning tank 104 from above through the opening 104a. Then, the cleaning liquid is injected into the cleaning tank 104 through the injection passage 104d and the injection port 104b and discharged through the discharge port 104c and the discharge passage 104e. Thus, the outer peripheral surface of the nozzle 111 is cleaned. Moreover, the cleaning liquid flows through the flow path 111b inside the nozzle 111. Thus, the inner peripheral surface of the nozzle 111, that is, the flow path 111b is cleaned.

As for the cleaning tank 104 and the nozzle 111, the same flow paths and mechanism as those in the case of the cleaning tank 41 and the nozzle 31 illustrated in FIG. 6B are formed. Except, as described above, the nozzle 111 dispenses a sample for use in blood coagulation test-related measurement only. A carry-over level in the blood coagulation test-related measurement is lower than that in the measurement for the immunological test. Therefore, in the case of the cleaning tank 104 and the nozzle 111, the first pump is omitted from the same flow path and mechanism as that illustrated in FIG. 6B, and a metering syringe may be used to cause the cleaning liquid to flow through the flow path 111b.

Alternatively, the cleaning tank 104 may be configured as illustrated in FIG. 7C. More specifically, in the cleaning tank 104 illustrated in FIG. 7C, an injection port 104b and an injection passage 104d are configured in the same manner as the injection port 41b and the injection passage 41d in FIG. 6A. Also, a discharge port 104c is formed in the bottom of the cleaning tank 104, and a discharge passage 104e extends downward. When a flow path 111b linearly extends downward in the same manner as the nozzle 111, the cleaning liquid flowing through the flow path 111b is discharged downward. Thus, the downward extending discharge passage 104e achieves smooth collection of the cleaning liquid.

Referring back to FIG. 3, the heating table 140 includes holding holes 141 for holding the reaction containers 22 and a transfer section 142 that transfers the reaction containers 22. The heating table 140 has a circular shape in a plan view and is configured to be rotatable in the circumferential direction. The heating table 140 heats the reaction container 22 set in a holding hole 141 to 37° C.

When a first sample is discharged into a new reaction container 22 held on the reaction container table 120, the reaction container table 120 is rotated and the reaction container 22 housing the first sample is transferred to near the heating table 140. Then, the transfer section 142 of the heating table 140 grabs the reaction container 22 and transfers the reaction container 22 to a holding hole 201a to be described later with reference to FIG. 8. On the other hand, when a second sample is discharged into a new reaction container 22 held on the reaction container table 120, the reaction container table 120 is rotated and the reaction container 22 housing the second sample is transferred to near the heating table 140. Then, the transfer section 142 of the heating table 140 grabs the reaction container 22 to set the reaction container 22 in the holding hole 141 of the heating table 140.

The reagent table 130 is configured to be capable of positioning reagent containers 131 each housing an adjusting reagent and a trigger reagent for use in blood coagulation test-related measurement. The reagent table 130 is configured to be rotatable in the circumferential direction. The reagent dispensers 161 and 162 dispense the reagent into the reaction containers 22 heated by the heating table 140.

To dispense the adjusting reagent into the reaction container 22, the transfer section 142 of the heating table 140 takes the reaction container 22 out of the holding hole 141 in the heating table 140 and sets the reaction container 22 at a predetermined position. Then, the reagent dispenser 161 or 162 aspirates the adjusting reagent from the reagent container 131 and discharges the aspirated adjusting reagent into the reaction container 22. Accordingly, the adjusting reagent is mixed into the sample. Thereafter, the transfer section 142 sets the reaction container 22 again in the holding hole 141 in the heating table 140.

To dispense the trigger reagent into the reaction container 22, the transfer section 106 takes the reaction container 22 out of the holding hole 141 in the heating table 140 and sets the reaction container 22 at a predetermined position. Then, the reagent dispenser 161 or 162 aspirates the trigger reagent from the reagent container 131 and discharges the aspirated trigger reagent into the reaction container 22. Accordingly, the trigger reagent is mixed into the sample to prepare a measurement specimen. Thereafter, the transfer section 106 sets the reaction container 22 in a holding hole 52a in the second measurement section 52.

The second measurement section 52 includes the holding holes 52a. The second measurement section 52 irradiates the reaction container 22 set in the holding hole 52a with light, and measures light transmitted through the measurement specimen or light scattered by the measurement specimen. Upon completion of the measurement of the measurement specimen in the reaction container 22, the reaction container 22 is disposed of through the disposal port 107 by the transfer section 106. The disposal port 107 includes a hole for disposing of the reaction container 22 that houses the measurement specimen measured by the second measurement section 52. The disposal port 107 is connected to a box that collects the reaction container 22 to be disposed of. The disposal port 107 enables smooth disposal of the reaction container 22 replaced on a sample-by-sample basis.

Figure 8:
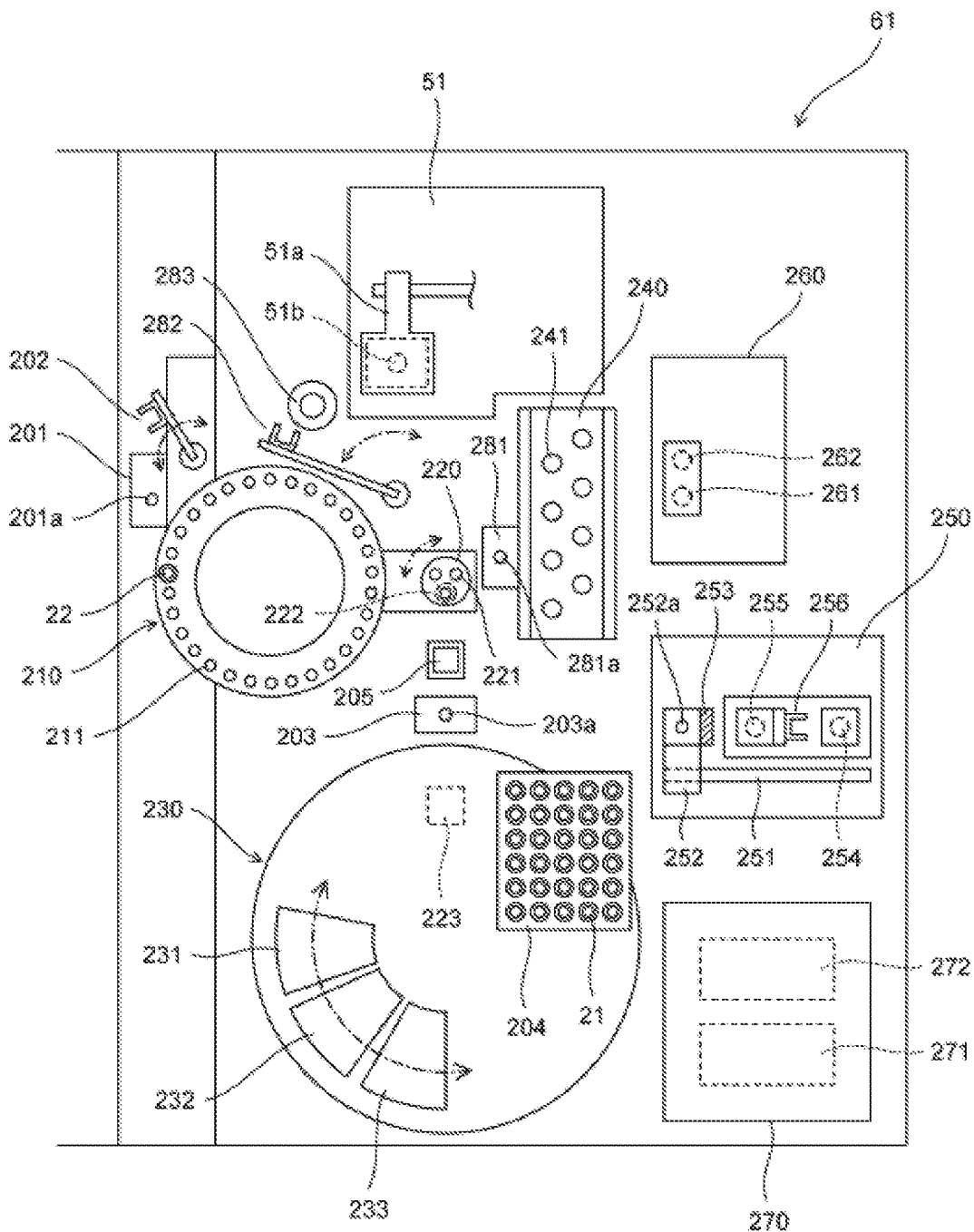
FIG. 8 is a diagram schematically illustrating a view of a configuration of a first measurement unit according to an embodiment.

As illustrated in FIG. 8, the first measurement unit 61 includes a member 201, a transfer section 202, handover tables 210 and 220, a member 203, a reaction container rack 204, a reagent table 230, a cleaning tank 205, a heater 240, a BF separator 250, a reagent dispenser 260, a reagent housing section 270, a member 281, a transfer section 282, a disposal port 283, and a first measurement section 51.

The member 201 includes a holding hole 201a for holding the reaction container 22. The transfer section 142 in the second measurement unit 62 takes the reaction container 22 housing a first sample out of the holding hole 121 in the reaction container table 120, and sets the reaction container in the holding hole 201a in the member 201. The handover table 210 includes holding holes 211. The handover table 210 has a circular shape in a plan view and is configured to be rotatable in the circumferential direction. The transfer section 202 takes the reaction container 22 out of the holding hole 201a and sets the reaction container 22 in the holding hole 211 in the handover table 210.

Figure 9:
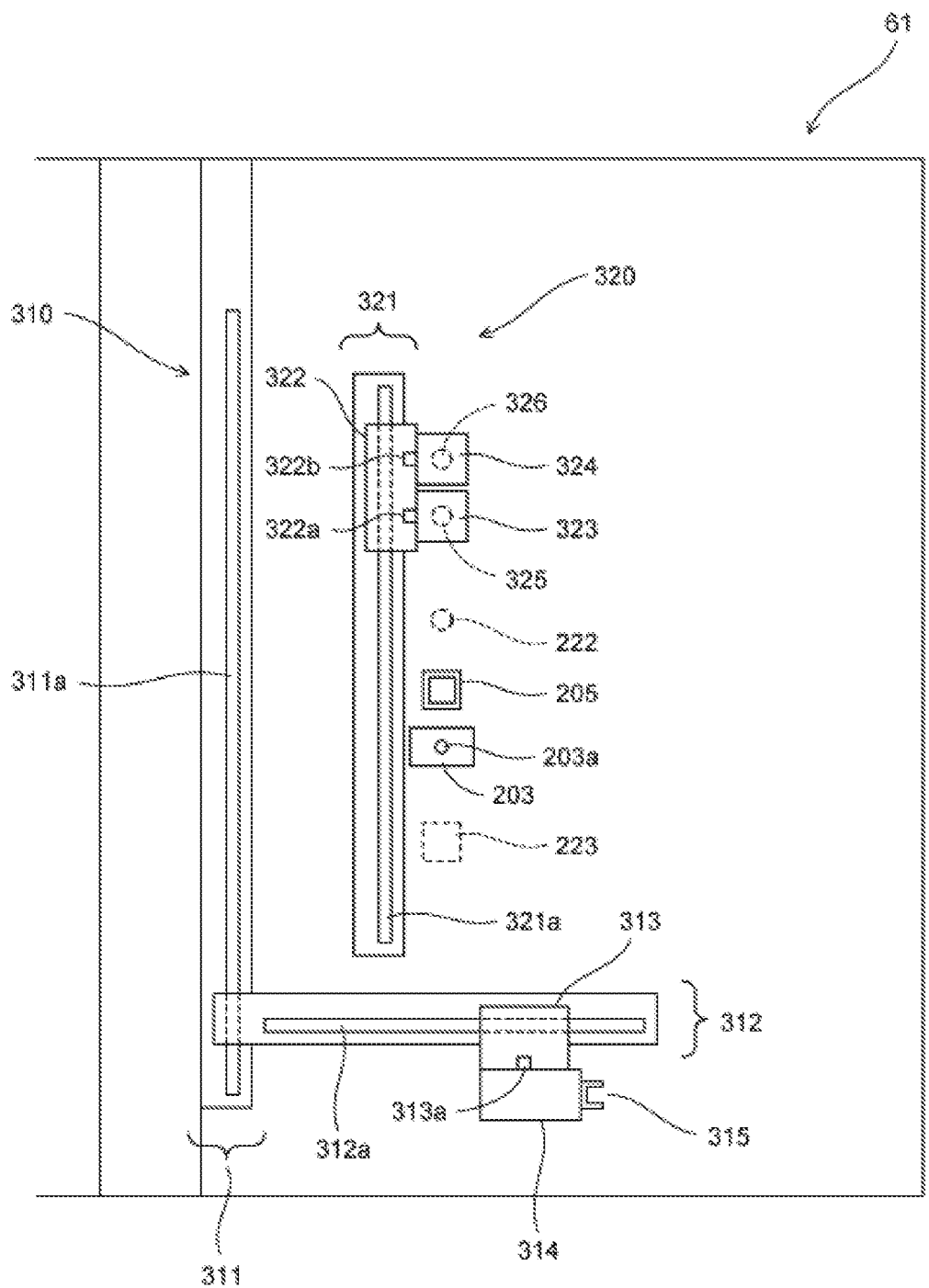
FIG. 9 is a diagram schematically illustrating a view of a configuration of a transfer section and a dispensing section in the first measurement unit according to an embodiment.

Here, the first measurement unit 61 includes a transfer section 310 and a dispenser 320 illustrated in FIG. 9, in addition to the parts illustrated in FIG. 8. The transfer section 310 is positioned on a wall surface in the first measurement unit 61, which is parallel to the Y-Z plane, while the dispenser 320 is positioned on a ceiling surface of the first measurement unit 61.

As illustrated in FIG. 9, the transfer section 310 includes a longitudinal transfer section 311, a horizontal transfer section 312, a vertical transfer section 313, a support member 314, and a grabber 315. The longitudinal transfer section 311 drives a stepping motor to transfer the horizontal transfer section 312 in the Y-axis direction along a rail 311a extending in the Y-axis direction. The horizontal transfer section 312 drives a stepping motor to transfer the vertical transfer section 313 in the X-axis direction along a rail 312a extending in the X-axis direction. The vertical transfer section 313 drives a stepping motor to transfer the support member 314 in the Z-axis direction along a rail 313a extending in the Z-axis direction. The support member 314 is provided with the grabber 315. The grabber 315 is configured to be capable of grabbing the reaction containers 21 and 22.

The transfer section 310 drives the longitudinal transfer section 311, the horizontal transfer section 312, and the vertical transfer section 313 to transfer the grabber 315 in the X-axis, Y-axis, and Z-axis directions within the first measurement unit 61. Thus, the reaction containers 21 and 22 can be transferred within the first measurement unit 61.

The dispenser 320 includes a longitudinal transfer section 321, a vertical transfer section 322, support members 323 and 324, and nozzles 325 and 326. The longitudinal transfer section 321 drives a stepping motor to transfer the vertical transfer section 322 in the Y-axis direction along a rail 321a extending in the Y-axis direction. The vertical transfer section 322 drives a stepping motor to transfer the support member 323 in the Z-axis direction along a rail 322a extending in the Z-axis direction and to transfer the support member 324 in the Z-axis direction along a rail 322b extending in the Z-axis direction.

The nozzles 325 and 326 are positioned in the support members 323 and 324, respectively, so as to line up in the Y-axis direction. The nozzles 325 and 326 extend in the Z-axis direction and have their tips pointed in the Z-axis forward direction. The nozzle 325 is used to dispense a sample, while the nozzle 326 is used to dispense a reagent.

As illustrated in FIG. 9, the nozzles 325 and 326, a sample aspirating position 222, the cleaning tank 205, a holding hole 203a, and a reagent aspirating position 223 are located in the same position in the X-axis direction. In other words, these members and positions are arranged in one straight line parallel to the Y-axis direction when seen in the Z-axis direction. Thus, the nozzles 325 and 326 can be located in the sample aspirating position 222, the cleaning tank 205, the holding hole 203a, and the reagent aspirating position 223 just by moving the nozzles 325 and 326 in the Y-axis direction without a mechanism to move the nozzles 325 and 326 in the X-axis direction. Thus, the configuration of the dispenser 320 can be simplified. Moreover, since the nozzles 325 and 326 can be cleaned with one cleaning tank 205, the cleaning tank 205 can be shared by the nozzles 325 and 326.

Note that flow paths inside the nozzles 325 and 326 extend in the vertical direction as in the case of the nozzle 111 in FIG. 7C. Therefore, the cleaning tank 205 also has the same shape as that of the cleaning tank 104 in FIG. 7C. In this case, the same mechanism and flow paths as those in FIG. 6B are configured to cause the cleaning liquid to flow into the nozzles 325 and 326 and the cleaning tank 205. Moreover, the first pump is driven to cause the cleaning liquid to flow into the nozzles 325 and 326 so that turbulent flows are generated inside the nozzles 325 and 326 during cleaning.

Referring back to FIG. 8, when a reaction container 22 is set in the holding hole 211 in the handover table 210, the transfer section 310 takes the reaction container 22 out of the holding hole 211 and sets the reaction container 22 in the holding hole 221 in the handover table 220. The handover table 220 includes three holding holes 221. The handover table 220 has a circular shape in a plan view and is configured to be rotatable in the circumferential direction. When the reaction container 22 is set in the holding hole 221 in the handover table 220, the handover table 220 is rotated in the circumferential direction to set the reaction container 22 in the sample aspirating position 222.

The reaction container rack 204 houses thirty new reaction containers 21. The member 203 includes a holding hole 203a for holding the reaction container 21.

The transfer section 310 takes the reaction container 21 out of the reaction container rack 204 and sets the reaction container 21 in the holding hole 203a. Then, the dispenser 320 uses the nozzle 325 to aspirate the first sample in the reaction container 22 set in the sample aspirating position 222 and discharge the aspirated first sample into the reaction container 21 set in the holding hole 203a. Thus, the first sample is transferred from the reaction container 22 to the reaction container 21. After the first sample is transferred, the nozzle 325 is cleaned in the cleaning tank 205. The reaction container 22 after completion of transferring of the second sample is disposed of through the disposal port 283 by the transfer section 282.

The disposal port 283 includes a hole for disposing of the reaction container 22 finished with moving of the sample and the reaction container 21 finished with the measurement by the first measurement section 51. The disposal port 283 is connected to a box that collects the reaction containers 22 and 21 to be disposed of. The disposal port 283 enables smooth disposal of the reaction containers 22 and 21 replaced on a sample-by-sample basis.

The reagent table 230 is configured to be capable of positioning reagent containers 231 to 233 each housing a reagent for use in measurement for an immunological test. The reagent table 230 is configured to be rotatable in the circumferential direction. The reagent container 231 houses R1 reagent, the reagent container 232 houses R2 reagent, and the reagent container 233 houses R3 reagent.

The transfer section 310 takes the reaction container 21 housing the first sample out of the holding hole 203a and sets the reaction container 21 above the cleaning tank 205. In this state, the dispenser 320 uses the nozzle 326 to aspirate R1 reagent from the reagent container 231 set in the reagent aspirating position 223 and discharge the aspirated R1 reagent into the reaction container 21 set above the cleaning tank 205. After R1 reagent is dispensed, the nozzle 326 is cleaned in the cleaning tank 205.

The heater 240 includes holding holes 241 for heating the reaction container 21. The transfer section 310 sets the reaction container 21 having R1 reagent discharged thereinto in the holding hole 241 of the heater 240. After the reaction container 21 is heated for a predetermined time by the heater 240, the transfer section 310 takes the reaction container 21 out of the holding hole 241 and sets the reaction container 21 above the cleaning tank 205. In this state, the dispenser 320 uses the nozzle 326 to aspirate R2 reagent from the reagent container 232 set in the reagent aspirating position 223 and discharge the aspirated R2 reagent into the reaction container 21 set above the cleaning tank 205. After R2 reagent is dispensed, the nozzle 326 is cleaned in the cleaning tank 205.

The transfer section 310 sets the reaction container 21 having R2 reagent discharged thereinto in the holding hole 241 of the heater 240. After the reaction container 21 is heated for a predetermined time by the heater 240, the transfer section 310 takes the reaction container 21 out of the holding hole 241 and transfers the reaction container 21 to the BF separator 250.

Here, R1 reagent contains a capturing substance to be connected with the test substance. R2 reagent contains magnetic particles. When R1 reagent and R2 reagent are discharged into the reaction container 21 and heated by the heater 240, the test substance contained in the first sample in the reaction container 21 is connected with the magnetic particles through the capturing substance by antigen-antibody reaction. As a result, a composite in which the test substance and the magnetic particles are connected with each other is generated.

The BF separator 250 includes a rail 251 extending in the X-axis direction, a support member 252 that moves along the rail 251, a magnet 253 positioned on the support member 252, a nozzle 254 for aspirating a liquid component in the reaction container 21, a nozzle 255 for discharging the cleaning liquid, and a grabber 256 for grabbing the reaction container 21. The BF separator 250 also includes a mechanism to transfer the support member 252 in the X-axis direction along the rail 251 and a mechanism to transfer the nozzles 254 and 255 and the grabber 256 in the Z-axis direction.

The transfer section 310 sets the reaction container 21 heated after discharging of R2 reagent in a holding hole 252a provided in the support member 252. The magnet 253 is positioned near the X-axis negative side of the holding hole 252a. Thus, in the reaction container 21 set in the holding hole 252a, the composite is drawn to a wall surface of the reaction container 21 on the X-axis negative side.

Subsequently, the reaction container 21 set in the holding hole 252a is positioned immediately below the nozzle 254. The nozzle 254 removes the liquid component from the reaction container 21. Then, the reaction container 21 set in the holding hole 252a is positioned immediately below the nozzle 255. The nozzle 255 discharges the cleaning liquid into the reaction container 21. Thereafter, the grabber 256 takes the reaction container 21 out of the holding hole 252a and agitates the reaction container 21 taken out through vibration. Upon completion of the agitation, the grabber 256 returns the reaction container 21 to the holding hole 252a. Then, the nozzle 254 removes the liquid component from the reaction container 21. The BF separator 250 repeats such operations.

Note that the BF separator 250 includes an unillustrated cleaning tank for cleaning the nozzle 254. This cleaning tank is positioned immediately below the nozzle 254 and has the same configuration as that of the cleaning tank 41 in FIG. 7A. The same mechanism and flow paths as those in FIG. 6B are configured to cause the cleaning liquid to flow into the nozzle 254 and the cleaning tank for cleaning the nozzle 254. Moreover, the first pump is driven to cause the cleaning liquid to flow into the nozzle 254 so that a turbulent flow is generated inside the nozzle 254 during cleaning. The nozzle 254 is cleaned upon every removal of the liquid component.

Subsequently, the transfer section 310 takes the reaction container 21 subjected to the processing in the BF separator 250 out of the holding hole 252a and sets the reaction container 21 above the cleaning tank 205. In this state, the dispenser 320 uses the nozzle 326 to aspirate R3 reagent from the reagent container 233 set in the reagent aspirating position 223 and discharge the aspirated R3 reagent into the reaction container 21 set above the cleaning tank 205. Then, the transfer section 310 sets the reaction container 21 having R3 reagent discharged thereinto in the holding hole 241 of the heater 240. After the reaction container 21 is heated for a predetermined time by the heater 240, the transfer section 310 takes the reaction container 21 out of the holding hole 241 and transfers the reaction container 21 to the BF separator 250. Then, the BF separator 250 performs the BF separation processing again.

Here, R3 reagent contains a labeling antibody in which an antibody is used as a capturing substance. When R3 reagent is discharged into the reaction container 21 and the reaction container 21 is heated by the heater 240, a composite in which the test substance, the capturing antibody, the magnetic particles, and the labeling antibody are connected with each other is generated.

Then, the transfer section 310 takes the reaction container 21 processed twice by the BF separator 250 out of the holding hole 252a and sets the reaction container 21 immediately below a nozzle 261 of the reagent dispenser 260. The reagent dispenser 260 includes the nozzle 261 for discharging R4 reagent and a nozzle 262 for discharging R5 reagent. The reagent dispenser 260 also includes a mechanism to transfer the nozzles 261 and 262 in the Z-axis direction.

The reagent dispenser 260 uses the nozzle 261 to discharge R4 reagent into the reaction container 21. Thereafter, the transfer section 310 sets the reaction container 21 having R4 reagent discharged thereinto immediately below the nozzle 262. The reagent dispenser 260 uses the nozzle 262 to discharge R5 reagent into the reaction container 21. Note that R4 reagent and R5 reagent are housed in reagent containers 271 and 272 provided in the reagent housing section 270, respectively, and the nozzles 261 and 262 are connected to the reagent containers 271 and 272, respectively, through unillustrated flow paths.

Here, R4 reagent is a reagent for dispersing the composite in the reaction container 21. When the composite is mixed with R4 reagent, the composite is dispersed in the reaction container 21. R5 reagent is a reagent containing a luminescent substrate that emits light by reaction with the labeling antibody connected with the composite. When the composite is mixed with R5 reagent, the labeling antibody connected with the composite reacts with the luminescent substrate to generate chemiluminescence. Thus, a measurement specimen for use in the first measurement is prepared.

The transfer section 310 sets the reaction container 21 having R5 reagent discharged thereinto in the holding hole 241 of the heater 240. After the reaction container 21 is heated for a predetermined time by the heater 240, the transfer section 310 takes the reaction container 21 out of the holding hole 241 and sets the reaction container 21 in a holding hole 281a provided in the member 281.

The first measurement section 51 includes a lid 51a and a holding hole 51b. The lid 51a is configured to be openable and closable above the holding hole 51b. When the reaction container 21 is set in the holding hole 281a, the lid 51a is opened and the transfer section 282 takes the reaction container 21 out of the holding hole 281a and sets the reaction container 21 in the holding hole 51b of the first measurement section 51. Then, the lid 51a is closed and light generated from the measurement specimen in the reaction container 21 is measured in the holding hole 51b. Upon completion of the measurement of the measurement specimen in the reaction container 21, the reaction container 21 is disposed of through the disposal port 283 by the transfer section 282.

Figure 10A:
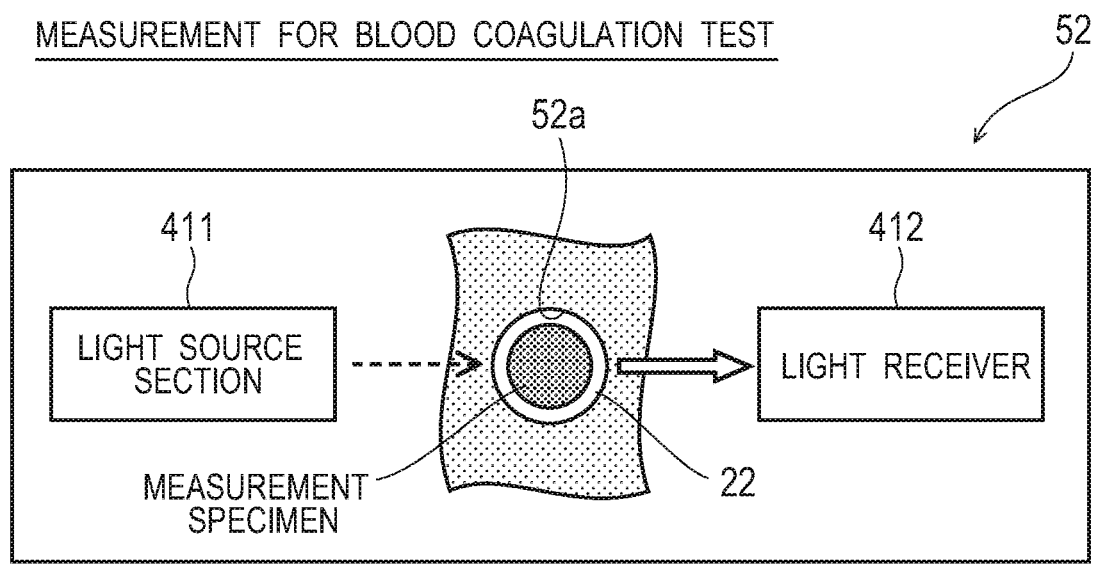
FIGS. 10A and 10B are diagrams schematically illustrating views of configurations of the second and first measurement sections, respectively, according to an embodiment.

As illustrated in FIG. 10A, the second measurement section 52 that performs blood coagulation test-related measurement includes a light source section 411 and a light receiver 412, in addition to the holding hole 52a described above. FIG. 10A illustrates the vicinity of one holding hole 52a.

The light source section 411 includes a semiconductor laser light source and emits light having different wavelengths. The light source section 411 irradiates the reaction container 22 set in each holding hole 52a with light. When the measurement specimen in the reaction container 22 is irradiated with light, light transmitted through the measurement specimen or light scattered by the measurement specimen enters the light receiver 412. The light receiver 412 is provided for each holding hole 52a and includes a photodetector. To be more specific, the light receiver 412 includes a photoelectric tube, a photodiode, and the like. The light receiver 412 receives transmitted light or scattered light and outputs an electric signal according to an amount of light received. Based on the electric signal outputted from the light receiver 412, the controller 62a generates measurement data for use in blood coagulation test-related analysis.

Note that, as described above, the second measurement unit 62 may perform biochemical test-related measurement. In this case, the second measurement section 52 has the same configuration as that for performing biochemical test-related measurement and blood coagulation test-related measurement. More specifically, also in the second measurement section 52 in this case, the light source section 411 irradiates the measurement specimen with light and the light receiver 412 receives transmitted light or scattered light generated from the measurement specimen. Then, based on an electric signal outputted from the light receiver 412, the controller 62a generates measurement data for use in biochemical test-related analysis.

Figure 10B:
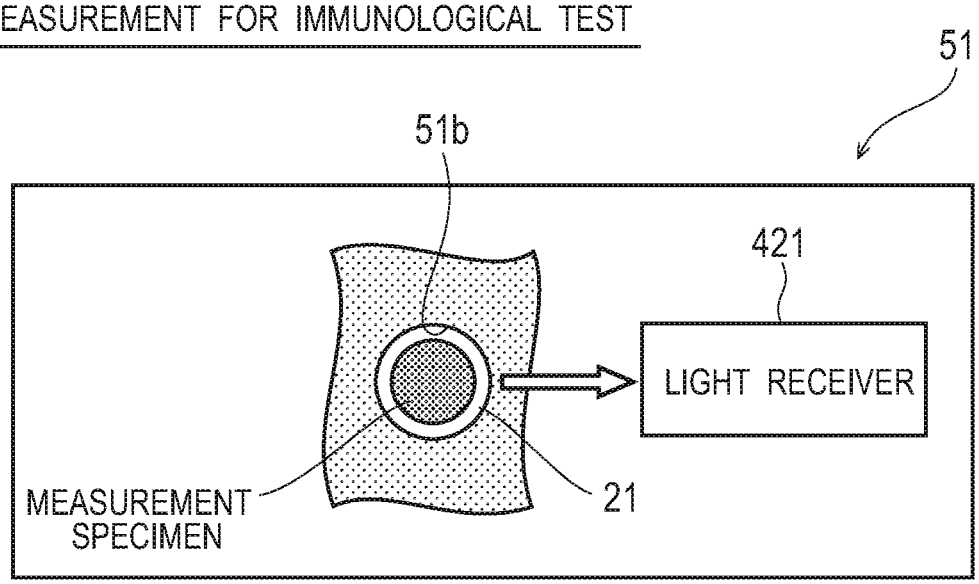

As illustrated in FIG. 10B, the first measurement section 51 that performs measurement for an immunological test includes a light receiver 421 in addition to the holding hole 51b described above. FIG. 10B illustrates the vicinity of the holding hole 51b.

The chemiluminescence generated from the measurement specimen housed in the reaction container 21 enters the light receiver 421. The light receiver 421 includes a photodetector capable of photon counting. To be more specific, the light receiver 421 includes a photomultiplier tube. When the light receiver 421 includes a photomultiplier tube capable of photon counting, the first measurement section 51 can perform highly sensitive and highly accurate measurement. The light receiver 421 receives the chemiluminescence and outputs a pulse waveform corresponding to photons received. The first measurement section 51 uses its internal circuit to count photons at regular intervals based on an output signal from the light receiver 421 and output a count value. Based on the count value outputted from the first measurement section 51, the controller 61a generates measurement data for use in immunological test-related analysis.

Figure 11:
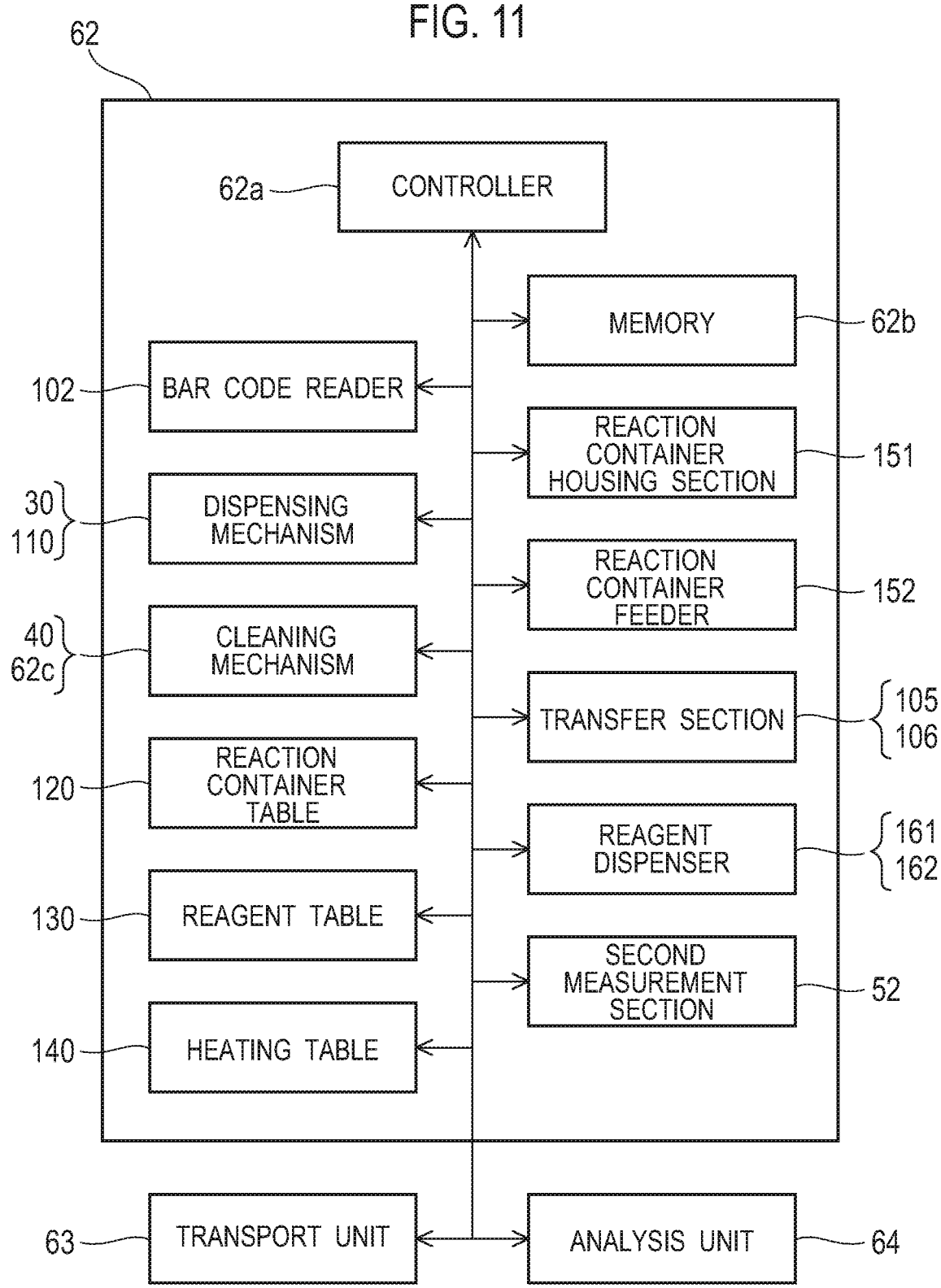
FIG. 11 is a diagram illustrating a view of a circuit configuration of the second measurement unit according to an embodiment.

As illustrated in FIG. 11, the second measurement unit 62 includes, as a configuration of a circuit section, the controller 62a, the bar code reader 102, the dispensing mechanisms 30 and 110, the cleaning mechanism 40, the reaction container table 120, the reagent table 130, the heating table 140, the reaction container housing section 151, the reaction container feeder 152, the transfer sections 105 and 106, the reagent dispensers 161 and 162, and the second measurement section 52, as described with reference to FIGS. 1 to 3. The dispensing mechanism 30 includes the sensor 35, the cleaner 36, and the drive sections 37 and 38 illustrated in FIG. 5.

As the configuration of the circuit section, the second measurement unit 62 also includes the memory 62b and a cleaning mechanism 62c. The controller 62a controls all the parts in the second measurement unit 62 and the transport unit 63 according to a program stored in the memory 62b. The memory 62b includes a ROM, a RAM, a hard disk, and the like. The cleaning mechanism 62c includes a cleaning tank 104 and flow paths and mechanism through which a cleaning liquid flows into the cleaning tank 104 and the nozzle 111.

Figure 12:
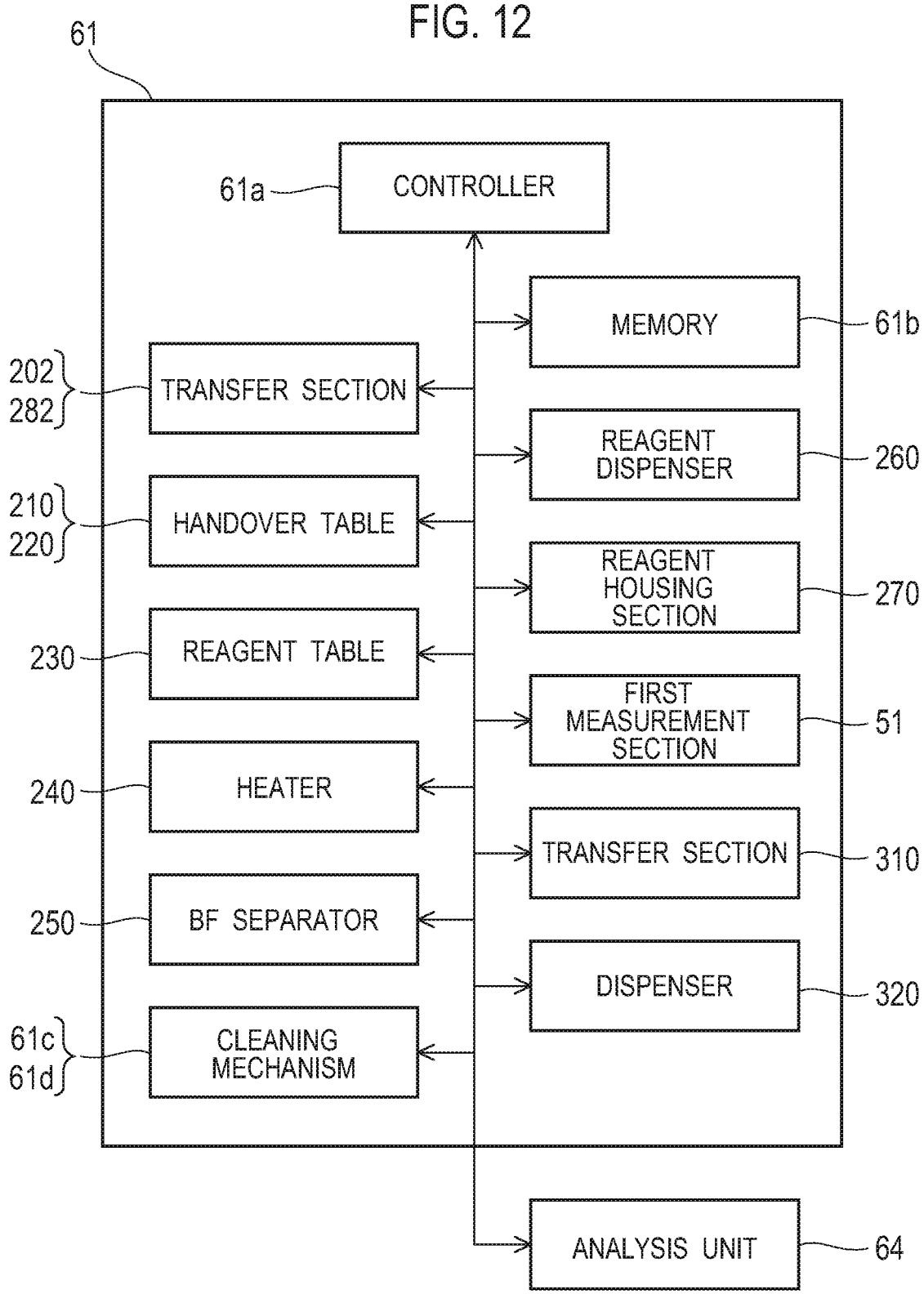
FIG. 12 is a diagram illustrating a view of a circuit configuration of the first measurement unit according to an embodiment.

As illustrated in FIG. 12, the first measurement unit 61 includes, as a configuration of a circuit section, the controller 61a, the transfer sections 202 and 282, the handover tables 210 and 220, the reagent table 230, the heater 240, the BF separator 250, the reagent dispenser 260, the reagent housing section 270, the first measurement section 51, the transfer section 310, and the dispenser 320, as described with reference to FIGS. 1, 2, 8 and 9.

As the configuration of the circuit section, the first measurement unit 61 also includes the memory 61b and cleaning mechanisms 61c and 61d. The controller 61a controls all the parts in the first measurement unit 61 according to a program stored in the memory 61b. The memory 61b includes a ROM, a RAM, a hard disk, and the like. The cleaning mechanism 61c includes a cleaning tank 205 and flow paths and mechanism through which a cleaning liquid flows into the cleaning tank 205 and the nozzles 325 and 326. The cleaning mechanism 61d includes a cleaning tank for cleaning the nozzle 254 in the BF separator 250 and flow paths and mechanism through which a cleaning liquid flows into the cleaning tank and the nozzle 254.

Figure 13:
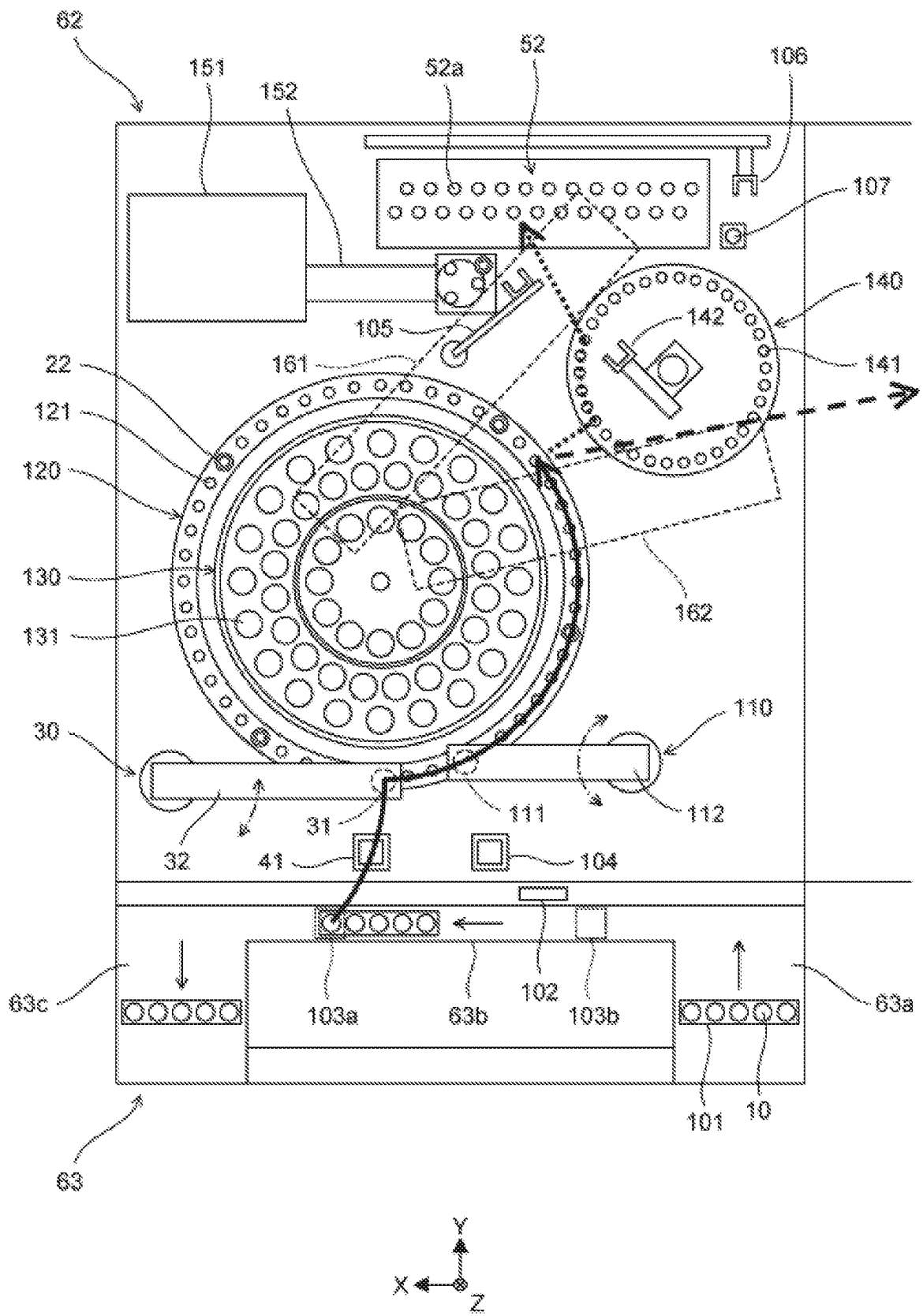
FIG. 13 is a diagram illustrating description of a transfer path of a sample within the second measurement unit according to an embodiment.

With reference to FIG. 13, description is given of a transfer path of a sample within the second measurement unit 62.

As illustrated in FIG. 13, the sample aspirated from the sample container 10 at the sample aspirating position 103a is discharged into the reaction container 22 on the reaction container table 120 by the dispensing mechanism 30, as indicated by the solid arrow. Then, as indicated by the solid arrow, the reaction container 22 having the sample dispensed therein is transferred to a position near the heating table 140 by the reaction container table 120.

When the sample housed in the reaction container 22 is the second sample, the reaction container 22 transferred to the position near the heating table 140 is transferred to the holding hole 141 in the heating table 140 by the transfer section 142 of the heating table 140. After an adjusting reagent is discharged into this reaction container 22, the reaction container 22 is set again in the holding hole 141. Thereafter, the reaction container 22 is transferred to the holding hole 52a in the second measurement section 52 from the holding hole 141 in the heating table 140 by the transfer section 106. The reaction container 22 in this case is transferred to the second measurement section 52 along a transfer path indicated by the dotted arrow.

On the other hand, when the sample housed in the reaction container 22 is the first sample, the reaction container 22 transferred to the position near the heating table 140 is transferred to the holding hole 201a in the first measurement unit 61 by the transfer section 142 of the heating table 140. The reaction container 22 in this case is transferred to the first measurement unit 61 along a transfer path indicated by the dashed arrow.

In this way, the reaction container 22 into which the second sample is dispensed by the dispensing mechanism 30 is transferred to the second measurement section 52 along the solid arrow and the dotted arrow. On the other hand, the reaction container 22 into which the first sample is dispensed by the dispensing mechanism 30 is transferred to the first measurement unit 61 along the solid arrow and the dashed arrow. More specifically, in the sample measurement device 100, a second transfer path along which the reaction container 22 having the second sample dispensed therein is transferred to the second measurement section 52 and a first transfer path along which the reaction container 22 having the first sample dispensed therein is transferred to the first measurement unit 61 are set. The first and second transfer paths include a transfer path in the section indicated by the solid arrow, as a common transfer path. When the first and second transfer paths include at least the common transfer path as described above, the sample measurement device 100 can be configured in a more compact manner than a case where the first and second transfer paths are two separate transfer paths.

Note that, although the first and second transfer paths include the common transfer path in the embodiment, those transfer paths may also be set as two completely separate transfer paths. Moreover, in the embodiment, a second transfer mechanism that transfers the reaction container 22 along the second transfer path includes the reaction container table 120 and the transfer sections 142 and 106, while a first transfer mechanism that transfers the reaction container 22 along the first transfer path includes the reaction container table 120 and the transfer section 142. Thus, although the first and second transfer mechanisms include a common mechanism in the embodiment, the disclosure is not limited thereto but the first and second transfer mechanisms may be configured as two completely separate mechanisms.

Figure 15A:
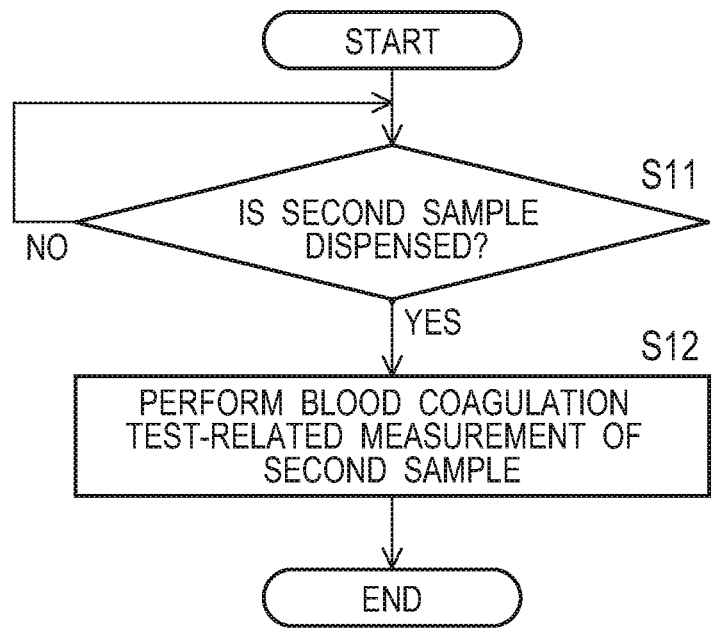
FIGS. 15A and 15B are flowcharts illustrating processing performed by the sample measurement device when a second sample and a first sample are dispensed, respectively, according to an embodiment.
Figure 15B:
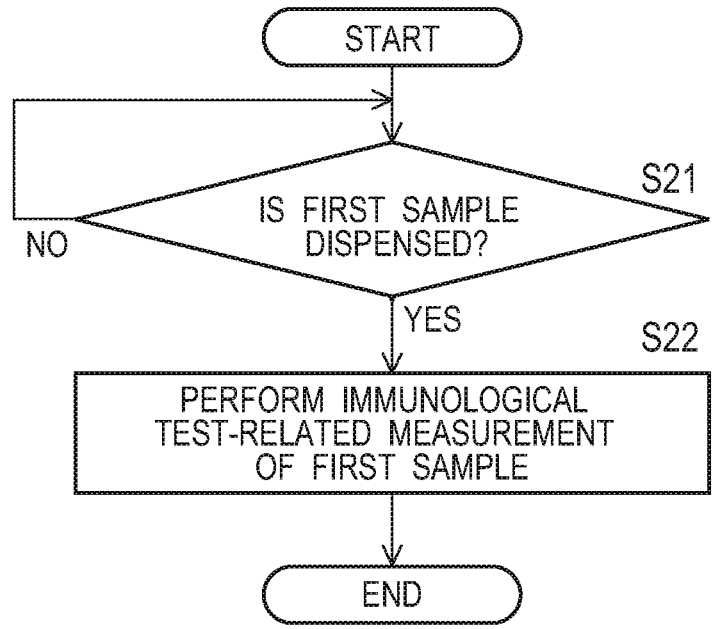
Figure 16:
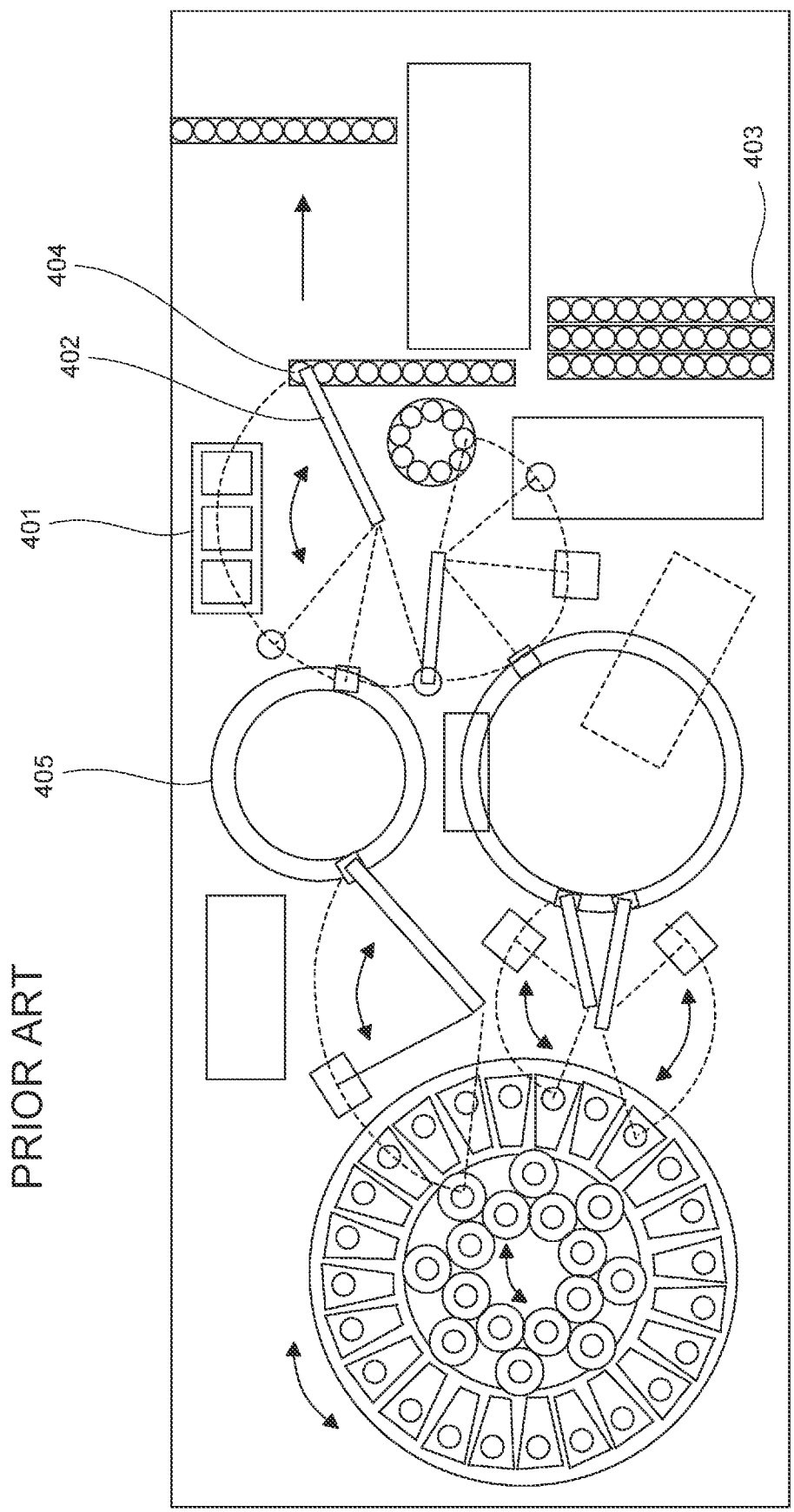
FIG. 16 is a diagram illustrating a schematic view of description of a configuration of the related technology.

With reference to flowcharts illustrated in FIGS. 14 to 15B, description is given of processing performed by the sample measurement device 100. FIG. 14 is a flowchart illustrating processing related to the dispensing mechanism 30. FIGS. 15A and 15B are flowcharts illustrating processing performed by the sample measurement device 100 when the second sample is dispensed and when the first sample is dispensed, respectively.

As illustrated in FIG. 14, when the sample measurement device 100 is started, the controller 62a drives the cleaning mechanism 40 to clean the nozzle 31 in the dispensing mechanism 30 in Step S1. Then, the sample container 10 is placed in the sample aspirating position 103a.

In Step S2, the controller 62a determines whether or not a measurement order related to a blood coagulation test is set for the sample in the sample container 10 placed in the sample aspirating position 103a. To be more specific, the controller 62a makes an inquiry to the analysis unit 64 about a measurement order based on the sample ID read by the bar code reader 102, and performs the determination in Step S2 based on the inquiry result.

When the blood coagulation test-related measurement order is set, the controller 62a drives the dispensing mechanism 30 in Step S3 to aspirate the sample in the sample container 10 and discharge the aspirated sample into a new reaction container 22 held by the reaction container table 120. The sample dispensed in Step S3 is a sample used for blood coagulation test-related measurement, which is the second sample as described above. On the other hand, when the blood coagulation test-related measurement order is not set, the processing in Step S3 is skipped.

In Step S4, the controller 62a determines whether or not a measurement order related to an immunological test is set for the sample in the sample container 10 placed in the sample aspirating position 103a. To be more specific, the controller 62a makes an inquiry to the analysis unit 64 about a measurement order based on the sample ID read by the bar code reader 102, and performs the determination in Step S4 based on the inquiry result.

When the measurement order for the immunological test is set, the controller 62a drives the dispensing mechanism 30 in Step S5 to aspirate the sample in the sample container 10 and discharge the aspirated sample into a new reaction container 22 held by the reaction container table 120. The sample dispensed in Step S5 is a sample used for the measurement for the immunological test, which is the first sample as described above. On the other hand, when the measurement order for the immunological test is not set, the processing in Step S5 is skipped.

To aspirate the sample in Steps S3 and S5, the controller 62a drives the drive section 37 to lower the nozzle 31 to penetrate through the plug body 11 and then further lower the nozzle 31. Thereafter, after sensing through the sensor 35 that the tip 31a of the nozzle 31 comes into contact with the liquid surface of the sample, the controller 62a drives the drive section 37 according to the number of pulses stored in the memory 62b to lower the tip 31a of the nozzle 31 by a predetermined amount from the liquid surface of the sample. Thus, the tip 31a is set in a position lower than the liquid surface by the predetermined amount. In this state, the controller 62a drives the dispensing mechanism 30 to aspirate the sample.

Upon completion of the dispensing processing thus performed on the sample container 10 placed in the sample aspirating position 103a, the processing returns to Step S1. In Step S1, the controller 62a drives the cleaning mechanism 40 to clean the nozzle 31 in the dispensing mechanism 30. Then, when the sample container 10 is placed in the sample aspirating position 103a, the controller 62a performs the processing in Steps S2 to S5.

As illustrated in FIG. 15A, the controller 62a determines in Step S11 whether or not the second sample is dispensed into the reaction container 22 on the reaction container table 120. When the second sample is dispensed into the reaction container 22, the controller 62a drives the respective parts of the second measurement unit 62 to perform processing such as heating and reagent dispensing for the reaction container 22 that houses the second sample, and then set the reaction container 22 in the holding hole 52a in the second measurement section 52. Thereafter, in Step S12, the controller 62a drives the second measurement section 52 to perform blood coagulation test-related measurement of the second sample. Upon completion of the second measurement in Step S12, the processing returns to Step S11.

As illustrated in FIG. 15B, the controller 62a determines in Step S21 whether or not the first sample is dispensed into the reaction container 22 on the reaction container table 120. When the first sample is dispensed into the reaction container 22, the controller 62a drives the respective parts of the second measurement unit 62 to transfer the reaction container 22 that houses the second sample to the holding hole 201a in the first measurement unit 61. Then, the controller 61a in the first measurement unit 61 drives the respective parts of the first measurement unit 61 to move the first sample to the reaction container 21 and perform processing such as heating, reagent dispensing, and BF separation for the reaction container 21 that houses the first sample before setting the reaction container 21 in the holding hole 51b in the first measurement section 51. Thereafter, in Step S22, the controller 61a drives the first measurement section 51 to perform immunological test-related measurement of the first sample. Upon completion of the first measurement in Step S22, the processing returns to Step S21.

<Other Configuration of Sample Measurement Devices>

Although, in the sample measurement device 100, the first measurement section 51 performs the immunological test-related measurement, the disclosure is not limited thereto but measurement for another test different from the immunological test may be performed, which is more highly sensitive than the test performed by the second measurement section 52. For example, in the sample measurement device 100, the first measurement section 51 may perform measurement for a genetic test.

Also when the first measurement section 51 performs the genetic test-related measurement, the sample container 10 that houses a sample is normally closed with the plug body 11. Therefore, generally, also in the genetic test-related measurement, the sample container 10 is fed to the sample measurement device 100 in a state where the top of the sample container 10 is opened by an operator removing the plug body 11 from the sample container 10, for example. In this case, the operator needs to previously go to the cumbersome work of removing the plug body 11 from the sample container 10.

However, also when the first measurement section 51 performs the genetic test-related measurement, again, the sample measurement device 100 dispenses the sample directly from the sample container 10 through the nozzle 31 as in the case where the first measurement section 51 performs the immunological test-related measurement. Thus, the operator needs not remove the plug body 11 from the sample container 10. Therefore, the genetic test-related measurement can be smoothly performed.

When carry-over occurs, an adequate measurement result for the genetic test can no longer be obtained. However, also when the first measurement section 51 performs the genetic test-related measurement, in the sample measurement device 100, the cleaning mechanism 40 cleans the nozzle 31 that dispenses the sample, as in the case where the first measurement section 51 performs the immunological test-related measurement. Thus, the influence of the carry-over can be reduced in the genetic test-related measurement. Moreover, also in this case, since the reaction container 22 into which the sample is dispensed is a disposable container that is replaced on a sample-by-sample basis, carry-over can be avoided, which is caused by mixing of different samples through the reaction container 22. Therefore, the genetic test-related measurement can be properly performed.

Note that the above embodiment also includes the following embodiment. More specifically, a chemiluminescence measurement device 100 includes: a dispensing mechanism 30 that includes a nozzle 31 capable of penetrating through a plug body 11 that closes a sample container 10 and of aspirating and discharging a sample housed in the sample container 10 closed with the plug body 11, and that dispenses the sample into a disposable container 20, 22 from the sample container 10 through the nozzle 31; and a first measurement section 51 that performs chemiluminescent measurement of the sample dispensed by the dispensing mechanism 30.

In the chemiluminescent measurement, measurement is performed by dispensing a sample from a sample container having its top open. However, with the use of the sample container having its top open, the sample may be condensed by evaporation of water content in the sample. Such condensation of the sample may affect the measurement result in the chemiluminescent measurement that is a highly sensitive measurement system.

Meanwhile, in the chemiluminescence measurement device described above, the sample container that houses the sample is closed with the plug body, and the sample is dispensed into a disposable container from the sample container by using the nozzle capable of penetrating through the plug body closing the sample container. Accordingly, evaporation of water content in the sample is suppressed. Thus, condensation of the sample can be prevented from affecting the measurement result. As a result, an adequate measurement result can be acquired based on the chemiluminescent measurement. Moreover, since the sample is dispensed through the nozzle penetrating through the plug body, the operator no longer needs to remove the plug body from the sample container closed with the plug body.

The disclosure includes other embodiments in addition to the above-described embodiments without departing from the spirit of the disclosure. The embodiments are to be considered in all respects as illustrative, and not restrictive. The scope of the disclosure is indicated by the appended claims rather than by the foregoing description. Hence, all configurations including the meaning and range within equivalent arrangements of the claims are intended to be embraced in the description.

The invention claimed is:

1. A sample measurement device comprising:
   a first dispensing mechanism comprising a first nozzle configured to be capable of penetrating through a plug body that closes a sample container and of aspirating and discharging a sample housed in the sample container, and configured to dispense the sample into a first disposable container of plural first disposable containers from the sample container through the first nozzle;
   a second dispensing mechanism comprising a second nozzle configured to be capable of aspirating and discharging the sample housed in the first disposable container, and configured to dispense the sample into a second disposable container of plural second disposable containers from the first disposable container into which the sample has been dispensed by the first dispensing mechanism through the second nozzle;
   a first cleaning mechanism located above a sample aspiration position where the first nozzle aspirates the sample in the sample container, the first cleaning mechanism comprising a vertically penetrating passage, the first cleaning mechanism configured to clean the first nozzle as the first nozzle passes through the passage;
   a second cleaning mechanism that comprises a first cleaning tank and is configured to clean the first nozzle;
   a third cleaning mechanism that comprises a second cleaning tank having an opening on a top thereof and that is configured to clean the second nozzle in the second cleaning tank;
   a first measurement section comprising a light receiver and configured to perform measurement for an immunological test of the sample in the second disposable container dispensed by the second dispensing mechanism from the first disposable container;
   a second measurement section comprising a second light receiver and configured to perform measurement for a test of the sample in the first disposable container dispensed by the first dispensing mechanism from the sample container, the test in the second measurement section being different from the immunological test in the first measurement section;
   a first controller configured, when it is determined that the sample is to be measured by the first measurement section and the second measurement section, to control the first dispensing mechanism to dispense the sample housed in the sample container into the plural first disposable containers and control the second measurement section to perform measurement for the test of the sample in one of the plural first disposable containers; and
   a second controller configured to control the second dispensing mechanism to dispense the sample housed in another of the plural first disposable containers into the second disposable container and control the first measurement section to perform measurement for the immunological test of the sample in the second disposable container dispensed from the another of the plural first disposable containers.

2. The sample measurement device according to claim 1, wherein
   the second cleaning mechanism is configured to clean at least portions of an inner peripheral surface and an outer peripheral surface of the first nozzle with cleaning liquid.

3. The sample measurement device according to claim 1, wherein
   the second cleaning mechanism comprises:
      the first cleaning tank including an injection port and an opening opened upwardly;
      a first pump that is configured to cause cleaning liquid to flow into the first nozzle; and
      a second pump that is configured to cause the cleaning liquid to flow into the injection port, and
   the first controller is configured, in a state where the first nozzle is inserted into the first cleaning tank through the opening, to control the second cleaning mechanism to drive the first pump to cause the cleaning liquid to flow into the first nozzle, and drives the second pump to cause the cleaning liquid to flow into the first cleaning tank from the injection port.

4. The sample measurement device according to claim 1, wherein
   the first controller is configured to control the second cleaning mechanism to clean the first nozzle on a sample-by-sample basis.

5. The sample measurement device according to claim 1, wherein
   the first controller is configured to replace the plural first disposable containers on a sample-by-sample basis.

6. The sample measurement device according to claim 1, wherein
   the first measurement section is configured to perform the measurement for the immunological test using antigen-antibody reaction.

7. The sample measurement device according to claim 1, wherein
   the first measurement section includes the light receiver that is configured to perform photon counting.

8. The sample measurement device according to claim 7, wherein
the first measurement section includes a photomultiplier tube.

9. The sample measurement device according to claim 1, wherein
the second measurement section is configured to perform measurement for a blood coagulation test or a biochemical test.

10. The sample measurement device according to claim 9, wherein
the second measurement section includes a light source section that irradiates a measurement specimen with light and the second light receiver that receives light generated from the measurement specimen.

11. The sample measurement device according to claim 1, wherein
the first dispensing mechanism is positioned closer to the second measurement section than to the first measurement section.

12. The sample measurement device according to claim 1, wherein
the first dispensing mechanism is configured to dispense the sample fed to the first measurement section from the sample container, and dispense the sample fed to the second measurement section from the sample container.

13. The sample measurement device according to claim 1, further comprising:
a first measurement unit in which the first measurement section is positioned; and
a second measurement unit in which the second measurement section is positioned, wherein
the first dispensing mechanism is positioned in the second measurement unit.

14. The sample measurement device according to claim 13, further comprising:
a first transfer mechanism that comprises a first transfer path to transfer the second disposable container that contains the sample dispensed from the another of the plural first disposable containers by the first dispensing mechanism, to the first measurement unit along the first transfer path; and
a second transfer mechanism that comprises a second transfer path to transfer the one of the plural first disposable containers, to the second measurement section along the second transfer path.

15. The sample measurement device according to claim 14, wherein
the first and second transfer paths include at least a common transfer path.

16. The sample measurement device according to claim 1, wherein
the first controller is configured to control the second cleaning mechanism to clean an inner peripheral surface of the first nozzle by causing a cleaning liquid to flow into the first nozzle at a predetermined rate to generate a turbulent flow inside the first nozzle.

* * * * *